United States Patent [19]
Babb et al.

[11] Patent Number: 5,364,917
[45] Date of Patent: Nov. 15, 1994

[54] PERFLUOROCYCLOBUTANE RING–CONTAINING POLYMERS

[75] Inventors: David A. Babb; W. Frank Richey; Katherine S. Clement, all of Lake Jackson, Tex.; Bobby R. Ezzell, Midland, Mich.

[73] Assignee: The Dow Chemical Company, Midland, Mich.

[21] Appl. No.: 159,892

[22] Filed: Dec. 1, 1993

Related U.S. Application Data

[60] Continuation-in-part of Ser. No. 54,648, Apr. 26, 1993, abandoned, which is a continuation-in-part of Ser. No. 929,742, Aug. 13, 1992, abandoned, which is a division of Ser. No. 673,882, Mar. 22, 1991, Pat. No. 5,159,038, which is a division of Ser. No. 364,667, Jun. 9, 1989, Pat. No. 5,037,917.

[51] Int. Cl.$^5$ ............ C08F 14/18; C08F 12/20; C08F 5/00; B29B 7/00
[52] U.S. Cl. .................. 526/242; 526/243; 526/244; 526/245; 526/247; 526/248; 526/250; 526/251; 526/252; 526/253; 526/255; 528/86; 264/328.1; 264/331.11; 264/331.19; 264/331.21
[58] Field of Search ......... 264/328.1, 331.11, 331.19, 264/331.21; 526/242, 243, 244, 245, 246, 247, 248, 250, 251, 252, 253, 255; 528/86; 568/669

[56] References Cited

U.S. PATENT DOCUMENTS

| | | | |
|---|---|---|---|
| Re. 23,425 | 10/1951 | Harmon | 570/132 |
| 2,848,504 | 8/1958 | Dixon | 570/132 |
| 3,505,411 | 4/1970 | Rice | 568/615 |
| 3,549,606 | 12/1970 | Gash | 252/247 |
| 3,900,380 | 8/1975 | Anderson et al. | 522/5 |
| 5,021,602 | 6/1991 | Clement et al. | 558/230 |
| 5,023,380 | 6/1991 | Babb et al. | 568/34 |
| 5,037,917 | 8/1991 | Babb et al. | 526/242 |
| 5,037,918 | 8/1991 | Babb | 526/242 |
| 5,037,919 | 8/1991 | Clement et al. | 526/242 |
| 5,066,746 | 11/1991 | Clement et al. | 526/242 |
| 5,159,036 | 10/1992 | Babb | 526/242 |
| 5,162,468 | 11/1992 | Babb et al. | 526/242 |
| 5,198,513 | 3/1993 | Clement et al. | 528/242 |
| 5,210,265 | 5/1993 | Clement et al. | 558/230 |

FOREIGN PATENT DOCUMENTS

| | | |
|---|---|---|
| 0303292 | 2/1989 | European Pat. Off. . |
| 0490335 | 6/1992 | European Pat. Off. . |
| 3024018 | 1/1981 | Germany . |
| 1126554 | 10/1968 | United Kingdom . |
| 1185564 | 3/1970 | United Kingdom . |
| 90/15042 | 12/1990 | WIPO . |
| 90/15043 | 12/1990 | WIPO . |
| 90/15044 | 12/1990 | WIPO . |
| 90/15082 | 12/1990 | WIPO . |

OTHER PUBLICATIONS

U.S. application Ser. No. 625,588 filed Dec. 10, 1990.
U.S. application Ser. No. 077,472 filed Jun. 15, 1993.
U.S. application Ser. No. 08/054,657 filed Apr. 26, 1993.

(List continued on next page.)

*Primary Examiner*—Peter Szekely

[57] ABSTRACT

A process for preparing a polymer having perfluorocyclobutane rings by the steps of (a) contacting monomers having aromatic polyester, aromatic polyamide, or polyimide groups or combination thereof, at least two dimerizable perfluorovinyl groups; and (b) exposing the monomers to sufficient heat and for a sufficient time that a polymer containing perfluorocyclobutane rings is formed. Chain extending oligomers of polymers having poor processing characteristics by this process results in polymers which are more easily processed. For instance, perfluorocyclobutane groups formed in an extruder to chain lengthen polyimide oligomers, in effect, render polyimides extrudable. The polymer formed by the method preferably has polyimide groups. New monomers and polymers having imide and perfluorovinyl or perfluorocyclobutane structures, respectively, are prepared.

23 Claims, No Drawings

OTHER PUBLICATIONS

Chem Abstract–105.171569h.

Prober "The Synthesis and Polymerization of Some Fluorinated Styrenes" in *J. Amer. Chem. Soc.* 75, pp. 968–973 (1953).

Henne et al. "Contrast in the Dimeriztion of Polychloro and Polyfluoro–ethylene" in *J. Amer Chem Soc* Feb. 1947 pp. 279–281.

Hauptschein et al "Thermal Syntheses of Telomers of Fluorinated Olefins Perfluoropropene" in *J. Amer. Chem, Soc.*, pp. 2549–2553 (1957).

Brown et al "Radiation–induced Polymerization and Other reactions of n–Perfluoropentadiene–1,4 at High Temperature and Pressure" in J. Poly. Sci. Part A–1, vol. 3, (1965), pp. 1641–1660.

Fearn et al "Polymers and Telomers of Perfluoro–1,-4–pentadiene" in J. Poly. Sci. Part A–1, vol. 34, (1966), pp. 131–140.

Banks et al "Polyhalogenoallenes, Part IV Thermal Co–dimerisation of Tetra–fluoroallene with Hexa-fluorobut–2–yne" in *J. Chem. Soc.* (1966) pp. 2051–2052.

Sharkey, "The Cycloaddition Reaction of Fluoroolefins" in *Fluorine Chem. Rev. (1968) pp. 1–53*.

Hodgdon et al. "Preparation and Polymerizability of Substituted a,B, B–Trifluorostyrenes" in J Poly Sci, vol. 6 (1968) pp. 711–717.

Chambers, Fluorine in Organic Chemistry, John Wiley, New York, (1973), pp. 173–188.

Rico et al., "Condensation of 1,2-Dibromotetrafluoroethane with Various Potassium Thiophenoxides and Phenoxides" in J. Fluorine Chem., (1982), pp. 759–764.

Heinze et al., "Palladium–Catalyzed Cross-Coupling of Perfluoroalkenylzinc Reagents with Aryl Iodides. A New Simple Synthesis of $\alpha,\beta,\beta$–Trifluorostyrenes and the Stereoselective Preparation of 1–Arylperfluoropropenes" in J. Org. Chem. (1988) pp. 2714–2720.

Paleta et al. "Haloacrylic Acids VI *Ethylene Glycol Bis(Trifluoroacrylate) in *Sb. Vsy.SkChem,.-Technol*" *(1976). pp. 5–11.*

Glazkov et al. "Cycloaddition of Perfluorovinyl Ethers to Dienes, " *Bulletin of the Academy of Scien.* USSR, (1988) pp. 2137–3141.

Tarrant et al. "The preparation and Reactions of Some Silanes Containing the Trifluorovinyl Group" In *J. Org. Chem.* vol. 31, No. 4, Apr. 1966, pp. 1143–1146.

PERFLUOROCYCLOBUTANE RING-CONTAINING POLYMERS

BACKGROUND OF THE INVENTION

This application is a continuation-in-part of U.S. application Ser. No. 08/054,648 filed Apr. 26, 1993, now abandoned, which is a continuation-in-part of U.S application Ser. No. 07/929,742 filed Aug. 13, 1992, now abandoned, which is a divisional application of U.S. application Ser. No. 07/673,882 filed Mar. 22, 1991, now U.S. Pat. No. 5,159,038, which is a divisional application of U.S. application Ser. No. 07/364,667 filed Jun. 9, 1989, now U.S. Pat. No. 5,037,917 all of which are incorporated by reference herein in their entireties.

This invention relates to polymerizations of perfluorovinyl compounds and to compositions containing more than one perfluorocyclobutane ring, more particularly to polymeric compositions containing more than one perfluorocyclobutane ring.

It has long been recognized that perfluorovinyl compounds having more carbon atoms than tetrafluoroethylene are very difficult to polymerize into aliphatic chains. Such difficulties are discussed, for instance in U.S. Pat. Nos. 2,848,504 and 2,958,685; and in *J. Polymer Science*, Part 1-A, pp. 481–492 (1952) and vol. 6, pp 711–717 (1968).

Dimerization of certain pedluorovinyl compounds has been reported and is discussed, for instance, in Chambers, *Fluorine in Organic Chemistry*, John Wiley, New York, 1973, pp. 173–191; S. Patai, *The Chemistry of Alkenes*, Wiley Interscience Publishers, 1964, p. 779; M. Hudlicky, *Chemistry of Organic Fluorine Compounds*, 2nd ed., Halsted Press (John Wiley and Sons), 1972, p. 450; and Tarrant ed., *Fluorine Chemistry Reviews*, Vol. 2, Marcel Dekker, 1968 pp. 1–52. In general, the dimerizations are easily sterically hindered and have not been used to prepare long chain molecules. A report of dimerization linking two molecules of such compounds as pedluoropropylene and perfluoropentene-1, included speculation that the reaction could be used for perfluoroalkyl perfluorovinyl compounds wherein the alkyl radical has 1 to 20, "or even a higher number" of carbon atoms. See, McCone et al., U.S. Pat. No. 3,316,312.

Such dimerization has not previously been reported to produce compounds having more than one perfluorocyclobutane ring. In fact, few compounds having multiple perfluorinated four carbon-rings have been reported. U.S. Pat. No. 3,303,145 discloses a number of polyethers formed from cyclic fluorocarbon epoxides, which polymers can have perfluorocyclobutane rings separated by oxygen atoms. The polymers are said to have good thermal stability and chemical inertness as well as dielectric properties. Use as solvents, heat-transfer media and lubricants as well as insulators in the form of films and moldings is suggested. U.S. Pat. No. 3,682,876 discloses polyperfluorocyclobutene and halogen terminated polypedluorocyclobutadienes. The solid polyperfluorocyclobutadienes are reported to be thermally stable, chemically inert and useful as coatings, ablatives, gaskets, bearings, potting compounds and sealants. U.S. Pat. No. 3,900,380 discloses polymers prepared by coupling certain perfluoroalkyl or perfluoroalkyl ether chains with iodine terminated perfluorocyclobutanes to prepare polymers having double bonds suitable for cross linking. The liquids are reported to be useful as hydraulic fluids, and the solids as gaskets and ablatives. Certain polymers containing radical-initiated rings, assumed for steric reasons to be four-membered rings are reported by Brown et al. in *J. Polymer Sci: Part A* vol. 3, pp 1641–1660 (1965) and vol. 4, pp 131–140 (1966). None of these reported polymers having perfluorocyclobutane rings is formed by thermal reaction of perfluorovinyl groups. Also, none has aromatic structure.

SUMMARY OF THE INVENTION

In one aspect the invention is a polymer having perfluorocyclobutane rings comprising the steps of:

(a) contacting monomers having at least two dimerizable perfluorovinyl groups; and (b) exposing the monomers to sufficient heat and for a sufficient time that a polymer containing perfluorocyclobutane rings is formed.

In another aspect the invention includes polymers formed by that process.

The process is of particular interest wherein the monomer has at least one imide group (a polyimide), particularly of a structure represented by Formula IV or V:

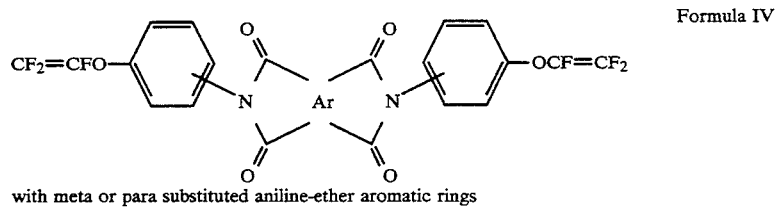

with meta or para substituted aniline-ether aromatic rings

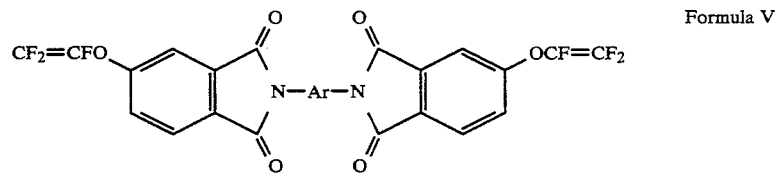

wherein Ar is an aromatic group; or

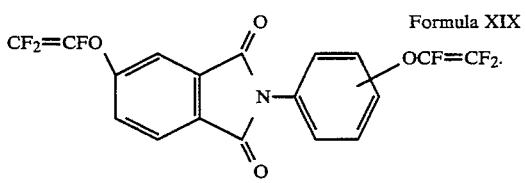

Monomers of Formulas IV, V and XIX and polymers comprising them are other aspects of the invention. The invention also includes methods of preparing monomers of Formula IV comprising (a) admixing a 4-aminophenyl trifluorovinyl ether or a 3-aminophenyl trifluorovinyl ether and an aromatic bis(anhydride) in a solvent which azeotropes with water and (b) azeotropically removing the water; and of Formula V comprising (a) contacting a 4-trifluorovinyloxyphthalic anhydride and an aromatic diamine in a solvent which azeotropes with water and (b) azeotropically removing the water. Also, monomers of Formulas IV, V, and XIX are prepared by mixing a 4-aminophenyl trifluorovinyl ether or a 3-aminotrifluorovinyl ether and an aromatic bis(anhydride) in a solvent, followed by the addition of a compound which chemically removes water, such as acetic anhydride. Other methods include (a) condensing aminoaromatic trifluorovinyl ethers or aminoaromatic(2-bromotetrafluoroethyl)ethers with aromatic bis(anhydrides), or (2-bromotetrafluoroethoxy)phthalic anhydrides with aromatic diamines, (b) imidizing the resulting amic acids by chemical means or by azeotropically removing water; and (c) reacting any 2-bromotetrafluoroethyl groups with zinc to form the corresponding trifluorovinyl compounds.

The polymers are useful, for instance, in such applications as those disclosed in U.S. Pat. No. 5,246,782.

DETAILED DESCRIPTION OF THE INVENTION

Polymers of the invention are formed by thermal reaction of monomers having at least two dimerizable perfluorovinyl groups such that perfluorocyclobutane groups are formed. A dimerizable perfluorovinyl group is a perfluorovinyl group which reacts with another such group to form a perfluorocyclobutane ring. Thus, resulting polymers have at least two perfluorocyclobutane groups, in particular sufficient perfluorocyclobutane groups to achieve physical and electrical properties desired for specific uses of the polymers. The term polymer is used herein to refer to any compound having at least two perfluorocyclobutane groups formed from perfluorovinyl groups, and includes oligomers which have from about 2 to about 100 repeating units and preferably have a weight average molecular weight of from about 300 to about 30,000. It is within the scope of the present invention to form lower weight average molecular weight oligomers useful as fluids or prepolymers and higher weight average molecular weight polymers exhibiting general plastic properties. Within this scope and depending on the molecular structure connecting the perfluorocyclobutyl groups, the number of perfluorocyclobutane groups can vary from as few as two up to thousands. The process of forming polymers or oligomers by the process of the present invention is general and capable of forming products having wide ranges of utility. Physical and electrical properties of the resulting products are highly dependent on the choice of the molecular structure between the perfluorocyclobutane groups as well as the number of perfluorocyclobutane groups.

The relative proportion by weight of the perfluorocyclobutane groups to the other molecular components of the resulting products can vary over a wide range of from about 12 to 1 to about 0.01 to 1, preferably from about 5 to 1 to about 0.02 to 1 and most preferably from about 2 to 1 to about 0.03 to 1. High proportions of perfluorocyclobutane groups are desirable for instance, when fluorocarbon character such as low dielectric constant is beneficial in the products. Exemplary of such products are low dielectric fluids and lubricants. Medium ranges of ratios of weights of perfluorocyclobutane groups to other molecular structures of about 2 to 1 to about 1 to 4 are desirable, for instance, when higher physical strength and relatively lower dielectric constants (e.g. relative to conventional engineering thermoplastics) are desired, e.g. in low dielectric plastics. These relatively low dielectric plastics are particularly preferred and are preferably achieved by using aromatic compounds substituted with trifluorovinyl groups, most preferably, with trifluorovinyl ether groups. Very low proportions of the perfluorocyclobutane groups result, for instance, when low weight average molecular weight oligomers (e.g. in the range of 1000 to 20,000) are terminated by trifluorovinyl groups and then thermally dimerized to form higher weight average molecular weight polymers.

Any monomer having at least two dimerizable perfluorovinyl groups is suitably used in the practice of the invention. Whereas polyaddition of perfluorovinyl groups to form perfluoroaliphatic polymers (like polytetrafluoroethylene), not generally having perfluorocyclobutane groups, takes place in the presence of free radicals or free radical generating catalysts, dimerization to form perfluorocyclobutane groups takes place thermally.

When a perfluorovinyl group is dimerizable, dimerization is preferably favored over other thermal reactions either kinetically or in equilibrium. In perfluorobutadiene, isomerization and formation of perfluorocyclobutane rings is favored; it is, therefore, preferable in the practice of the invention that the perfluorovinyl groups on a monomer used in the practice of the invention be separated by at least one atom or group of atoms, which group does not facilitate isomerization. The atom or group of atoms preferably includes at least one carbon atom, more preferably at least one carbon atom in an, optionally substituted, hydrocarbyl group, that is a group containing at least one carbon-hydrogen bond for instance a methylene group, a phenylene group, a phenylene ether group, a pyridinyl group and the like. Furthermore, when the perfluorovinyl groups are attached to aliphatic carbons or separated from aliphatic carbons by single atoms such as oxygen, the perfluorovinyl groups are preferably primary or secondary because tertiary perfluorovinyl groups are generally sterically hindered with respect to formation of perfluorocyclobutane rings, more preferably the perfluorovinyl groups are primary because secondary perfluorovinyl groups tend to rearrange. Preferably, to avoid rearrangement and facilitate polymer formation the monomers have structures such that resulting polymers have hydrocarbyl groups (preferably aromatic rings), perfluorocyclobutane rings and at least one non-carbon atom such as oxygen, silicon, boron, phosphorus, nitrogen, selenium, tellurium and/or sulfur atom (each optionally substituted) in the backbones.

The monomers preferably have a structure represented by Formula I:

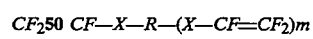

$CF_2$=$CF$—$X$—$R$—$(X$—$CF$=$CF_2)_m$ wherein R represents an, optionally inertly substituted group; each X is independently a bond or any group which links R and a perfluorovinyl group (hereinafter linking structures), said structures being inert; m+1 is the number of —X—CF=CF$_2$ units. Advantageously, m is an integer of from about 1 to about 3, preferably from about 1 to about 2. By "inert" it is meant that the structures or substituents do not react undesirably with perfluorovinyl groups or interfere undesirably with polymerization (perfluorocyclobutane formation) of the monomers.

Linking structures X are each independently a linking structure such as a bond, an oxygen atom, carboxylic and thiocarboxylic ester groups, other sulfur containing structures, perfluoroalkylene, perfluoroalkylene ether, alkylene, acetylene, phosphorus containing groups such as phosphines, carbonyl and thio carbonyl groups; seleno; telluro; nitrido; silicon-containing groups such as silanediyl, trisilanediyl tetrasilanetetrayl, siloxanediyl, disiloxanediyl, trisiloxyl, trisilazanyl, or silylthio groups; boron-containing groups such as boranediyl or methylboranediyl groups; a combination thereof, or any other group which is inert, which molecularly links R to a perfluorovinyl group, and which provides a molecular structure in which the perfluorovinyl group is sufficiently reactive to form a perfluorocyclobutane ring. For instance, X is preferably other than a perfluoroalkylene group because perfluorovinyl groups attached to perfluoroalkylene groups generally require temperatures greater than about 300° C. to dimerize and are subject to isomerization.

It is preferred that at least one of X is not a bond. More preferably, X is independently selected from the group consisting of groups having at least one non-carbon atom between the perfluorovinyl groups and R, such as groups containing oxygen, sulfur, selenium atoms, tellurium atoms, silicon, boron, phosphorus or nitrogen between R and the perfluorovinyl group, e.g. oxygen atoms, sulfur atoms, (thio) carboxylic ester groups, phosphines, (thio) carbonyl groups, seleno, telluro, silanediyl, trisilanediyl, trisilazanyl or silylthio, boranediyl groups. Preferred groups have S, O, Si, N or P, more preferably S, O, or Si between R and the perfluorovinyl group, such as carbonyl, thiocarbonyl, sulfone, sulfoxy, silanediyl, amines (optionally inertly substituted), oxygen or sulfur atoms. Most preferably there is a single atom other than carbon; even more preferably it is oxygen or sulfur, among those groups preferably an ether or sulfide linkage, because monomers having such linking structures advantageously form perfluorocyclobutane groups at lower temperatures than are needed with such groups as perfluoroalkyl groups and are more stable than monomers where the perfluorovinyl group is attached directly to R, particularly when R is aromatic. Monomers having such linking structures are also relatively easily prepared.

R is suitably any inert molecular structure, preferably a molecular structure which facilitates formation of perfluorocyclobutane rings and/or imparts desirable physical properties to polymers or oligomers prepared from the monomers. For the purpose of imparting desirable physical properties to polymers, R preferably contains at least one carbon atom. Preferably, the carbon atom is in the molecular chain between X's because monomers having at least one carbon atom between X's when X is other than a bond, tend to have desirable stability and to produce polymers having desirable physical properties. Alternatively, the carbon atom is in a side chain; for instance, —R—can be —N(CH$_3$)—, —N(CH$_2$CH$_3$)——P(CH$_3$)—, —P(CH$_2$CH$_3$)—and the like. The carbon atoms(s) in R are suitably in aliphatic, cycloaliphatic, aromatic, heterocyclic groups and the like and combinations thereof. Additionally, R optionally contains groups or has substituents which are inert, that is which do not undesirably interfere with the formation of perfluorocyclobutane rings from perfluorovinyl groups. Inert substituents include ether, carbonyl, ester, tertiary amide, carbonate, sulfide, sulfoxide, sulfone, nitrile, alkyl phosphonate, tertiary amine alkyl phosphate, alkyl silyl, chlorine, bromine, fluorine, alkyl, arylalkyl, alkylaryl, cycloalkyl, aromatic, heterocyclic, alkoxyl, aryloxy groups and the like, which inert substituents are suitably in any position, for instance, in a polymer backbone between X's and/or appended to such a backbone. Carbon-containing inert substituents on R preferably contain from about 1 to about 50, more preferably from about 1 to about 12 carbon atoms because of the stability and ease of working with monomers of lower weight average molecular weight. R, including inert substituents preferably has a weight average molecular weight (MW) of from about 14 to about 20,000, more preferably from about 75 to about 15,000 and most preferably from about 75 to about 5,000. These ranges include monomeric and oligomeric R groups. In the case of monomers which are other than oligomeric, R preferably has from about 1 to about 50, more preferably from about 6 to about 25, carbon atoms because weight average molecular weights above this reduce the contribution to properties made by the fluorine-containing substituents when R is alkyl or aromatic hydrocarbon. As previously discussed, the nature of R as well as the perfluorocyclobutane content of the polymers can vary broadly according to the type of products desired.

Preferably, for polymers having good plastic properties such as tensile strength and flexibility, at least one carbon atom of R is in the molecular chain between X's and is part of an aromatic nucleus. Aromatic groups are desirable because of improved physical properties of the polymers and ease of manufacture of the monomers. For both ease of manufacture of the monomer and monomer stability, when R is aromatic, each X is preferably independently sulfur or oxygen. The aromatic group can be any molecular structure having aromatic character, advantageously having at least one six membered aromatic ring, suitably having any number of such six-membered rings fused together or connected by bonds or linking structures. R preferably has from about 1 to about 50 such rings, more preferably from about 1 to about 10 rings, more preferably containing from about 6 to about 25 carbon atoms, most preferably R has at least 2 to about 4 aromatic rings to impart properties such as hardness and/or stiffness to a polymer. The aromatic fragment is suitably unsubstituted or inertly substituted. Inert substituents on an aromatic R include, for instance, the inert substituents listed for R generally. Exemplary aromatic molecular fragments include, for instance, perchlorophenylene, phenylene, biphenylene, naphthylene, dichlorophenylene, nitrophenylene, p,p'(2,2-diphenylene propane) [—C$_6$H$_4$—C(CH$_3$.)$_2$—C$_6$H$_4$]; p,p'—(2,2-diphenylene-1,1,1,3,3,3 hexafluoropropane) [—C$_6$H$_4$—C(CF$_3$)$_2$—C$_6$H$_4$]—,preferably biphenylene; phenylene; benzophenone, 9,9'-diphenylfluorene, oxydiphenylene; thiodiphenylene; 2,2-diphenylene propane; 2,2'-diphenylene, 1,1,1,3,3,3-hexafluoropropane; 1,1-diphenylene-1-phenylethane; naphthalene; and anthracene. Weight average molecular weights of aromatic ring containing polymers are preferably at least about 10,000. Such aromatic groups are preferably present because they generally impart high temperature glass transition properties (Tg) and good mechanical strength (e.g. as measured by differential scanning calorimetry (DSC) and tensile/flexural tests) to the polymer.

Most preferably, at least one aromatic carbon atom of R is bonded directly to X, most preferably aromatic carbon atoms of R are bonded directly to each X because perfluorovinyl groups bonded to X, said X being bonded to aromatic groups are generally more reactive in forming perfluorocyclobutane rings.

Some specific combinations of X and R are especially preferred: when R is aromatic, at least one X is preferably other than a bond, more preferably neither X is a bond, because attachment of perfluorovinyl groups directly to aromatic R renders the perfluorovinyl groups more thermally and oxidatively unstable than when said groups are attached, for instance to oxygen or sulfur. When R is a perfluoroalkyl group or a perfluoroalkylether group, at least one X is preferably other than a bond, most preferably no X is a bond or a perfluoroalkyl group, because perfluorovinyl groups linked directly to perfluoroalkyl groups require temperature in excess of about 300° C. to dimerize and are subject to isomerization.

Monomers useful in the practice of the invention are suitably prepared by any method which links molecular structures having perfluorovinyl groups to other molecular structures or which forms perfluorovinyl groups.

Perfluorovinyl groups are formed, for instance by elimination of halogens from terminal dihalotrifluoroethyl groups. Halogens such as bromine or iodine may be eliminated, for instance, using metallic reactants as illustrated by Cohen's systhesis of trifluorostyrene by the reaction of zinc with dichlorotrifluoroethylbenzene in absolute ethanol (J. Am. Chem. Soc., 71, 3439, (1949)). Additionally, pentafluoroethyl (substituted) phenyl ethers can be reacted with certain phosphorus compounds to form perfluorovinyl ethers as reported by Kawaguchi et al. in Japanese Kokai 77 89,603. Structures suitable for elimination of halogens to form perfluorovinyl groups are prepared, for instance, by processes such as those taught in Rico et al. U.S. Pat. No. 4,377,711 and Carl et al. in U.S. Pat. No. 4,423,249 which patents are incorporated herein by reference. Additionally perfluorovinyl groups are formed by decarboxylation of pedluorocarboxylic acids with concomitant loss of hydrogen fluoride, as taught by R.N. Griffin and M.I. Bro, J. Org. Chem., 25, 1068 (1960), and also by T.S. Reid, G.H. Smith, and W.H. Pearlson, in U.S. Pat. No. 2,746,997 which are incorporated herein by reference. Electrochemical elimination of halogens from certain substituted alkyl-1,2-dihalo-1,2,2-trifluoroethyl ethers according to the procedures taught in European Patent document EP 293,856 is also useful for forming perfluorovinyl compounds.

Tetrafluoroethylene and chlorotrifluoroethylene are reacted with suitable compounds, for instance by procedures taught by Prober in J. Amer. Chem. Soc., 75, 968 (1953); by Plumer et al. (U.S. Office Saline Water, Res. Develop. Prog. Rep. #481, 1969); by Dixon in J. Org. Chem., 21,400 (1956); Wall et al. U.S. Pat. No. 3,277,068.

Linking of molecular structures containing perfluorovinyl groups to other molecular structures is illustrated by reaction of (trifluorovinyl)trimethyltin aryl iodides in the presence of palladium complexes, as taught by R.S. Sorokina, et al. in Zh. Org. Khim., 18, 2458, (1982); by the reaction of trifluorovinyl zinc reagents with certain substituted phenyl iodides as taught by R.S. Sorokina et al. in Izv. Akad. NaUk SSSR, Ser. Khim., 1647, (1985); and Heinze and Burton in J. Fluorine Chem., 31, 115, (1986), and J. Org. Chem., 53, 2714, (1988).

Preferred monomers are preferably prepared by the process taught in U.S. Pat. No. 5,023,380 issued on Jun. 11, 1991 or by processes taught in U.S. application Ser. No. 07/625,588 filed Dec. 10, 1990, issued as U.S. Pat. No. 5,246,782 on Sep. 4, 1993 which is incorporated herein by reference in its entirety.

Imide monomers of the present invention are advantageously prepared by processes taught therein including fluoroalkylation of a phenolic starting material with 1,2-dibromotetrafluoroethane and subsequent reaction with zinc, for instance, in acetonitrile, to form the corresponding trifluorovinyl compounds. Phenolic starting materials are optionally unsubstituted or inertly substituted phenolic compounds. In the present invention, preferred substitution includes an amino group, or functionality which is convertible to a functional group useful in the present invention, for instance 3,4-dimethyl groups which are oxidizable to a carboxylic acid anhydride functionality, or a nitro group which is chemically reducible to an amine. The amine and carboxylic groups are then incoporated into imides.

When the fluoroalkylation products do not have the amine or anhydride functionality preferred to form imides, the preferred reactions include at least one step of further reacting the fluoroalkylated product to generate a chemical functionality which is preferred in the present invention, for instance oxidation of 3,4-dimethyl groups to a carboxylic acid anhydride, or reduction of a nitro group to an amino group. This step optionally involves multiple chemical reactions within the skill in the art, such as nitration of an unsubstituted fluoroalkylated phenol to provide a nitroaromatic fluoroalkyl ether, the nitro group of which is then reduced to an amino group useful in the present invention.

The imides are preferably prepared by general methods 1, 2, 3, 4, 5 and 6:

Method 1

A 3- or 4-Aminophenyl trifluorovinyl ether is combined with an aromatic bis(anhydride) in solution in the presence of a solvent which azeotropes with water, and the imidization reaction is carried out by the azeotropic removal of water according to the following general formula:

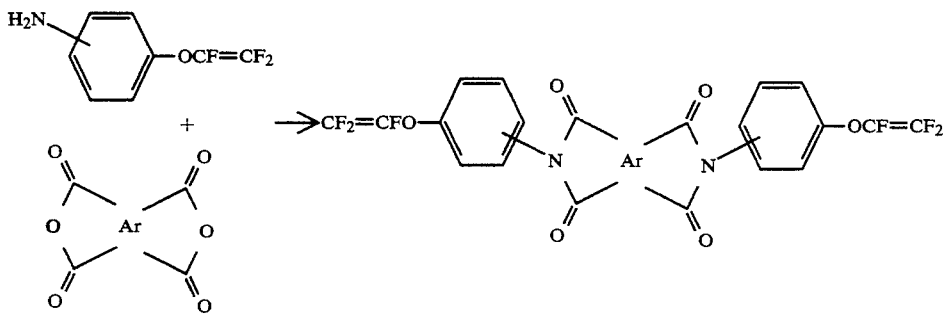

Formula IVa wherein Ar is an aromatic group preferably having from 1 to about 10, more preferably from 1 to about 5 aromatic rings either fused or otherwise linked, and optionally heterocyclic but preferably carbocyclic; such as phenylene, benzophenone, biphenylene, oxydiphenylene, 9,9-bis(phenyl)fluorene, spiro[fluorene-9,9'-xanthene], naphthalene, 2,2-bis(phenyl)hexafluoropropane (referred to in the art as 6F), 1,1,1-tris(phenyl)-trifluoroethane) (referred to in the art as 3F) and the like. The aromatic group is unsubstituted or inertly substituted, that is having substituents which do not undesirably affect the formation of the perfluorocyclobutane ring.

Method 2

4-Trifluorovinyloxyphthalic anhydride is combined with an aromatic diamine in solution in the presence of a solvent which azeotropes with water, and the imidization reaction is carried out by the azeotropic removal of water according to the following general formula:

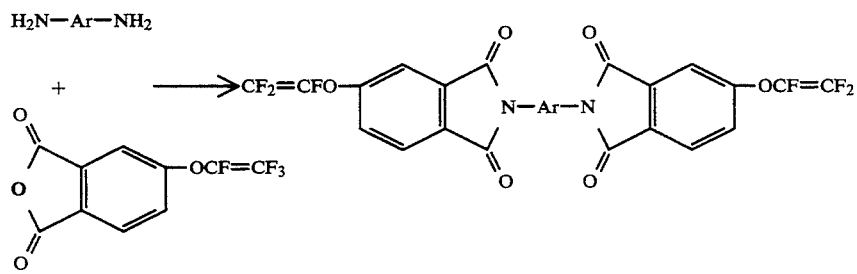

Formula Va wherein Ar is as defined for Formula IVa.

Method 3

A 3- or 4- aminophenyl trifluorovinyl ether is combined with an aromatic bis(anhydride) preferably in solution in the presence of a chemical agent which removes water, such as acetic anhydride, and the imidization reaction is carried out by chemical means, according to the general representation of Formula IVa. A process of imidization by chemical means involves adding a chemical agent which removes water to form a solution of a monomer in the amic acid form. This chemical agent then dehydrates the amic acid to form the corresponding imide and the hydrolyzed form of the chemical agent. For example, the addition of acetic anhydride to a solution of the movement of Formula XIX (in the amic acid form) in dimethyl acetamide produces the monomer of Formula XIX and two equivalents of acetic acid. (See C.P. Yang and J. H. Lin, Journal of Polymer Science, Part A: Polymer Chemistry, 31,2153–2163 (1993). The reaction is preferably carried out in any solvent for the bis(anhydride) and aminophenyltrifluorovinyl ether including N,N-dimethylformamide, N,N-dimethylacetamide, diglyme, tetraglyme. Chemical agents which remove water include acetic anhydride, propionic anhyd ride, maleic an hydride, malonic anhydride. Preferred bis(anhydrides) are ones which provide a combination of high temperature stability and good mechanical properties such as high flexural strength including biphenyl dianhydride, pyromellitic dianhydride, benzophenone dianhydride, 9,9-bis(3,4-dicarboxylic anhydride) fluorene, 1,2 bis( 1,3-isobenzofurandion-5-oxy) hexafluorocyclobutane, and the like.

Method 4

4-Trifluorovinyloxyphthalic anhydride (i.e. 5-(trifluorovinyloxy)-1,3-isobenzofuran dione) is combined with an aromatic diamine preferably in solution in the presence of a chemical afient which removes water, such as acetic anhydride, and the imidization reaction is carried out by chemical means, according to the general representation of Formula Va. Preferred solvents, chemical agents which remove water and imidization are as for Method 3. Preferred aromatic diamines have at least one aromatic ring and more preferably from 1 to about 8 rings, at least 2 amine groups primary, preferably 1 to about 6 aromatic rings, most preferably 1 to 4 aromatic rings. Preferred diamines include 1,4-diaminobenzene, 1,3-diaminobenzene, 4,4'-diaminobiphenyl, 4,4'oxydianiline, 3,3'-oxydianiline, 9,9-bis(4-aminophenyl fluorene.

Method 5

A 3- or 4- aminophenyl (2-bromotetrafluoroethyl) ether is combined with an aromatic bis(anhydride) in solution in the presence of a solvent which azeotropes with water, or a chemical agent which removes water, such as acetic anhydride, and the imidization reaction is carried out by either the azeotropic removal of water or by chemical means. The resulting N-(2-bromotetrafluoroethoxy)phenyl phthalimide containing compound is then reacted with zinc in e.g. acetonitrile or glyme solvent to convert the 2-bromotetrafluoroethoxy functionality to a trifluorovinyl ether functionality.

such as that published in *Polymer Preprints*, 33, (1), 203, (1992), an example of which is provided in Example 32 of the instant invention.

Formula IV

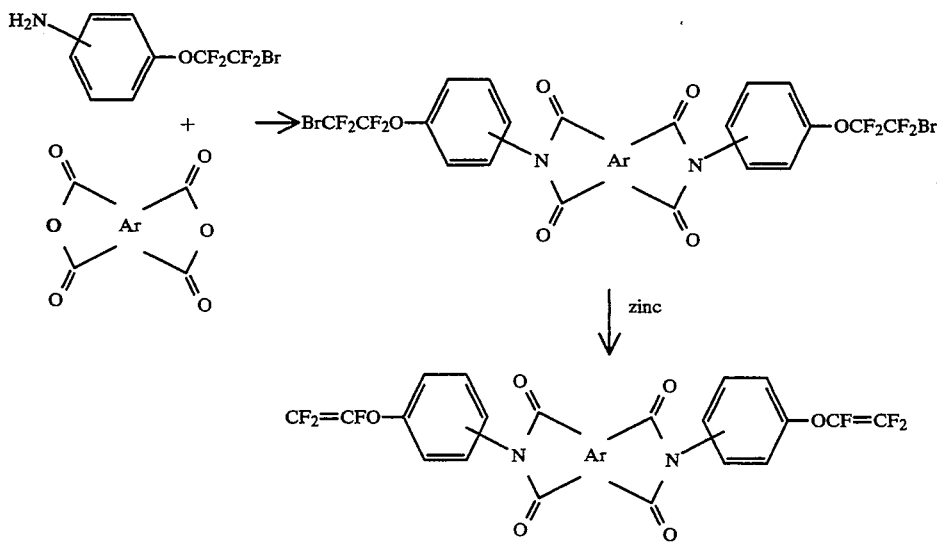

wherein Ar is as defined for Formula IVa.

Method 6

4-(2-Bromotetrafluoroethoxy)phtalic anhydride is combined with an aromatic diamine in solution in the presence of a solvent which azeotropes with water or a chemical agent which removes water, such as acetic anhydride, and the imidization reaction is carried out by either the azeotropic removal of water or by chemical means. This 2-bromotetrafluoroethoxyphthalimide containing compound is then reacted with zinc in e.g. acetonitrile or glyme solvent to convert the 2-bromotetrafluoroethoxy functionality to a trifluorovinyl ether functionality.

The steps of each method are carried out in the sequence listed, or alternatively carried out in a different sequence, according to the methods preferable for compatibility of the chemical reactions. One example of a different sequence is Example 41 of the instant invention, in which combination of an amine with a carboxylic acid anhydride is carried out before conversion of the 2-bromotetrafluoroethyl ether to a trifluorovinyl ether functionality.

In each method the reactants are either unsubstituted or inertly substituted, that is substituted with groups which do not undesirably interfere with formation of the compounds or its use as a monomer. Such groups include methoxy, nitro, halogen, or aromatic ether Formula V

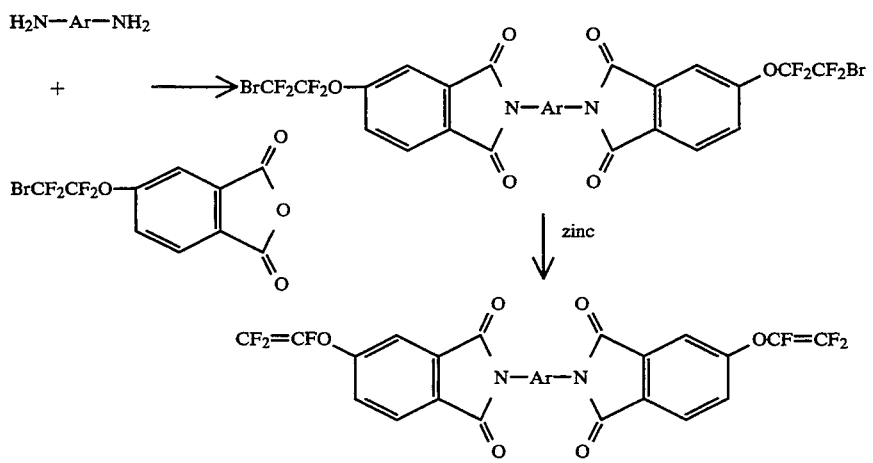

In general these methods involve reactions of a fluoroalkylated phenolic compound, either an amine or anhydride, with an anhydride (to react with an amine) or amine (to react with an anhydride) to form a compound having at least one imide functionality and at least one fluoroalkyl group. This reaction is optionally carried out by azeotropic removal of water, as in Methods 1 and 2 or alternatively may be carried out by chemical imidization, by a method within the skill in the art groups.

Polymers produced from the preferred monomers preferably have a formula represented by Formula II:

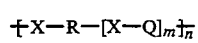

wherein R, X, and m, are defined above, Q is a perfluorocyclobutane group; and n is an integer representing the number of repeating units, which is preferably from about 2 to about 100,000. More preferably from about 2 to about 10,000, most preferably from about 3 to about 5,000. More preferably m is one or two. Formula II is generalized; when m is greater than one some of the —X—Q structures represent branching and/or crosslinking.

The monomers are heated to a temperature and for a time sufficient to form perfluorocyclobutane rings. Temperatures suitable for forming perfluorocyclobutane rings differ with the structure of the monomer. In general, temperatures above about 40° C. are suitable for formation of perfluorocyclobutane rings, preferably the temperature is above about 50° C., more preferably above about 100° C., because these temperatures result in formation of the rings at successively faster rates. Temperatures above about 450° C. are preferably avoided because perfluorocyclobutane groups are generally thermally unstable above such temperatures. More preferably a temperature of from about 105° C. to about 350° C., most preferably from about 105° C. to about 250° C., is used to produce the perfluorocyclobutane rings at a convenient rate. Within that range, a temperature of from about 100° to about 230° is generally most preferred for cyclization of perfluorovinyl aromatic or aliphatic ethers or sulfides, while a temperature of from about 50° C. to 80° C. is needed to form perfluorocyclobutane groups when the perfluorovinyl group is attached directly to an aromatic ring. In the case of perfluoroalkylperfluorovinyl groups, however, temperature of at least about 300° C., preferably at least about 350° C., is generally required.

Preferably, especially when the perfluorovinyl compounds are capable of radical initiated addition polymerization, conditions conducive to free radical polymerization, e.g. presence of oxygen, ozone, peroxygen compounds and other free radical generating compounds are avoided so that the pedluorovinyl groups will dimerize into perfluorocyclobutane groups rather than undergoing addition polymerization. Compounds known in the art for stabilization against free radical polymerization are alternatively used. Similarly, especially when the perfluorovinyl groups are capable of addition polymerization in the presence of anions or cations, compounds which supply such anions or cations are avoided. For instance, fluoride ions (e.g. from carbonyl fluorides) chloride, hydroxide, phenoxide and the like are preferably avoided. To avoid such compounds as carbonyl fluorides, oxidative conditions such as presence of oxygen, hypochlorite, dichromate, permanganate and the like are preferably avoided because perfluorovinyl groups are known to oxidize to form carbonyl fluorides. Perfluorovinyl ethers, thioethers, sulfones, sulfoxides and the like are relatively stable with regard to addition polymerization and oxidation; and, therefore, such precautions are generally unnecessary when such perfluorovinyl compounds are used.

Monomers or admixtures thereof are suitably neat or, optionally, in admixture with other materials such as in solution, in emulsion, in dispersions or in any other form in which monomer molecules can be contacted with one another to form a polymer. Liquid admixtures are advantageous for maintaining contact between monomer molecules such that higher weight average molecular weight polymers are formed. This is particularly useful when linear thermoplastic polymers are the products. Neat polymerization is preferred when the monomers or prepolymers are formed in the final desired shape of the polymer article before final thermal treatment. This is especially true when monomers having more than two perfluorovinyl groups are used in whole or in part to formed crosslinked, thermoset materials. Neat polymerizations or oligomerizations are also generally preferred to form relatively low weight average molecular weight fluid products.

Suitable solvents are those which are inert to the conditions encountered in the polymerization reaction and include perfluorotetradecahydrophenanthrene (MULTIFLUOR® APF 215 commercially available from Air Products Corp.). At atmospheric pressure, preferred solvents are those which attain temperatures of 170°–250°C. such as dichlorobenzene, trichlorobenzene, diphenyl oxide, mesitylene, and perfluorotetradecahydrophenanthrene. Although solvents such as 1,2-dichlorobenzene and 1,2,4-trichlorobenzene give less satisfactory results such as discoloration of the finished polymer, they are suitably used when their disadvantages are tolerable in a final product. When a solvent is used the concentration of monomers in solvent is advantageously from about 0.1 to about 99.9 weight percent preferably, from about 10 to about 90 percent by weight monomer.

Polymerization or dimerization suitably takes place at any pressure. Pressures are generally chosen such that the monomers and any solvents and/or dispersing media remain liquid at the temperatures used for polymerization. When the monomers or other materials evaporate at temperatures used, then it is generally preferable to maintain a pressure at least sufficient to maintain the materials liquid.

In a preferred embodiment of the invention, conditions suitable for all or part of the dimerization can occur in a polymer shaping apparatus, for instance, an extruder, injection mold or compression mold. This embodiment of the invention is particularly useful when materials containing perfluorovinyl groups, for instance, monomers, oligomers or polymers, have a viscosity suitable for introducing into the polymer shaping apparatus and the material resulting from the formation of perfluorocyclobutane groups in the apparatus has a higher viscosity or is solid, which is less suitable for introduction into the apparatus. More specifically, a perfluorovinyl containing oligomer or relatively lower weight average molecular weight polymer, including the result of partial dimerization of perfluorovinyl groups or, preferably, other polymerization reactions (including addition or condensation polymerizations), is introduced into a shaping apparatus wherein it is heated sufficiently for formation of sufficient perfluorocyclobutane rings to form a solid polymer. This technique is particularly useful when applied to oligomers of materials that would be difficult to fabricate as high weight average molecular weight polymers, but where the properties of the higher weight average molecular weight polymers are desired.

One such preferred embodiment of the invention suitable for, but not limited to, formation of perfluorocyclobutane rings in a shaping apparatus involves forming trifluorovinyl terminated relatively low weight average molecular weight (e.g. from about 300 to about 30,000, preferably from about 1000 to about 20,000, more preferably from about 1000 to about 5000) oligomers or polymers, that have a low viscosity relative to their higher weight average molecular weight counterparts, suitably low weight average molecular weight polymers of the present invention, addition polymers (including addition polymers of perfluorovinyl compounds) or condensation polymers such as polyethers, poly(carboxylic acid derivatives) including polyesters, polyurethanes, epoxy resins, polysulfones, polycarbonates and polyamide-polyimides; preferably polycarbonates, polyesters, polyamides, polyimides and the like, more preferably polyimides, liquid crystal polymers, especially polyesters, aromatic polyesters, aromatic polyamides, aromatic polycarbonates and the like which are frequently intractable or have high melting points and poor melt flow characteristics above temperatures commonly used in shaping or molding polymers, when advanced to high weight average molecular weights such as weight average molecular weights greater than about 10,000. These materials are advantageously prepared from the oligomers or polymers by forming the trifluorovinyl group directly onto the terminal positions using chemistry such as taught in the preceding paragraphs or, more conveniently, by reacting a compound containing a trifluorovinyl group and a second functional group reactive with the terminal functionality of the oligomers or polymers. Examples of suitable second functional groups on the compound containing the trifluorovinyl group are carboxylic acid groups and their derivatives such as salts, acid halides, or esters; amines, either primary or secondary; hydroxyl; chloroformate or any number of other nucleophilic or electrophilic groups. Suitable terminal groups of the oligomers or polymers are the same as described for the trifluorovinyl containing compound. When one of the reactants has a given reactive group, the other has a functional group of opposite reactivity, i.e. nucleophilic with electrophilic. Preferably the perfluorovinyl group is incorporated as a perfluorovinyl ether, more preferably a perfluorovinyl aromatic ether, most preferably as the perfluorovinyl ether of an aromatic ester, as for example $CF_2=CF-O-Ar-CO-O-$oligomer where Ar is an aromatic group. An example of the latter method of preparing the monomer and subsequently the polymer of the present embodiment of the invention is the reaction of polycarbonate oligomer or other oligomer having terminal phenolic groups with 4-trifluorovinyloxybenzoyl chloride. The resulting oligomeric monomer is terminated with trifluorovinyl groups connected to the oligomer via ester groups formed in the reaction of the phenolic end groups with the acid chloride reactive site of the trifluorovinyl compound. The reaction is conveniently conducted by methods of forming esters from phenolics and acid chlorides. Oligomers, thus capped, are then thermally polymerized to a high weight average molecular weight polymer wherein the oligomer fragments are linearly linked by perfluorocyclobutane rings. Polymers, thus formed, retain substantial property similarity to high weight average molecular weight resins of the oligomer structure. Preparation of trifluorovinyl compounds having second functional groups are prepared according to procedures outlined above and taught in U.S. Pat. No. 5,037,919 issued Aug. 6, 1991 and U.S. Pat. No. 5,021,602, respectively, which are incorporated by reference herein in their entireties. The 4-trifluorovinyloxybenzoyl chloride referred to above and related compounds are prepared from phenolic substituted aromatic esters by techniques taught in U.S. Pat. No. 4,423,249, which is incorporated herein by reference, followed by hydrolysis to the acid and then conversion to the corresponding acid chloride. The above technique is equally applicable to polyfunctional compounds other than oligomers of polymers. Thus a difunctional compound such as dihydroxybiphenyl can be reacted with the above acid chloride to form a bis(trifluorovinyl) monomer.

Polyimide oligomers are of particular interest because the process of the invention provides a facile way to make easily processsible polyimides having high Youngs modulus, preferably at least about 350,000; more preferably at least about 400,000, most preferably at least about 500,000 psig (2,413,165 kPa; 2,757,902 kPa; 3,447,379 kPa, respectively). In a preferred embodiment the oligomers have a repeating unit corresponding to at least one of the following formulas:

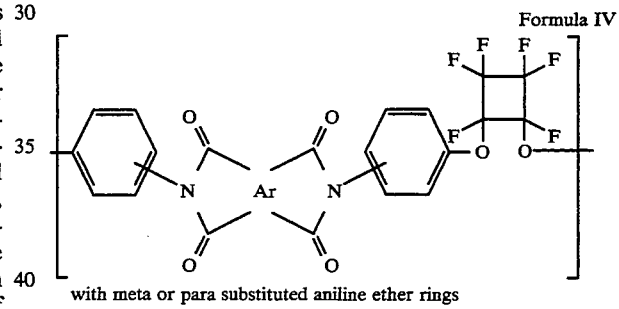

with meta or para substituted aniline ether rings

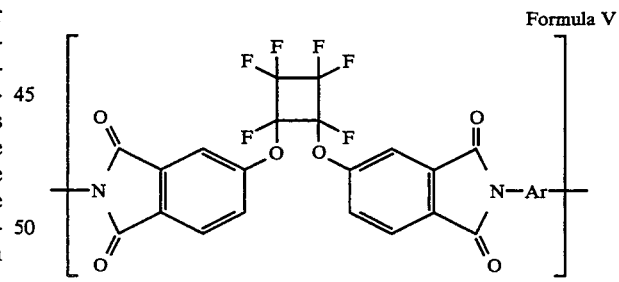

These repeating units are derived from monomers with the following structural formulas:

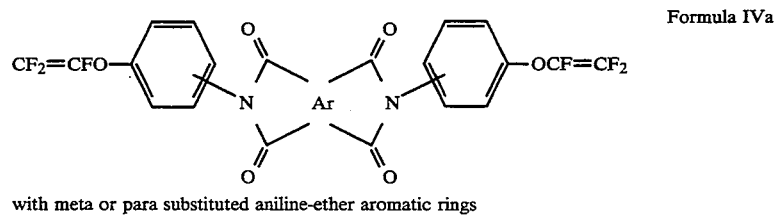

with meta or para substituted aniline-ether aromatic rings

Formula Va
Preferred repeating units from monomers of Formula IVa or Va include:
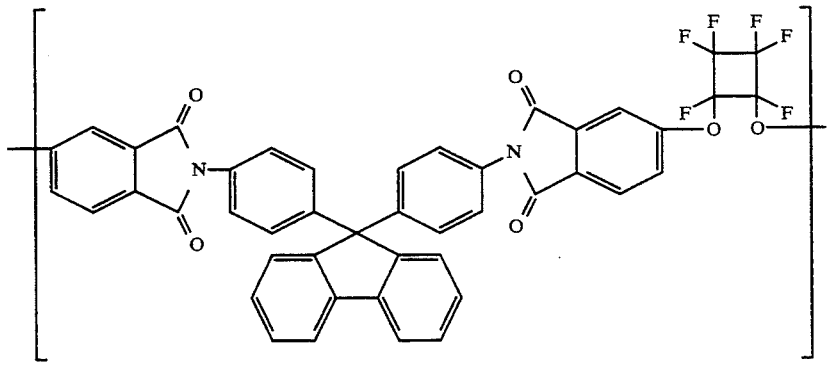
Formula VI
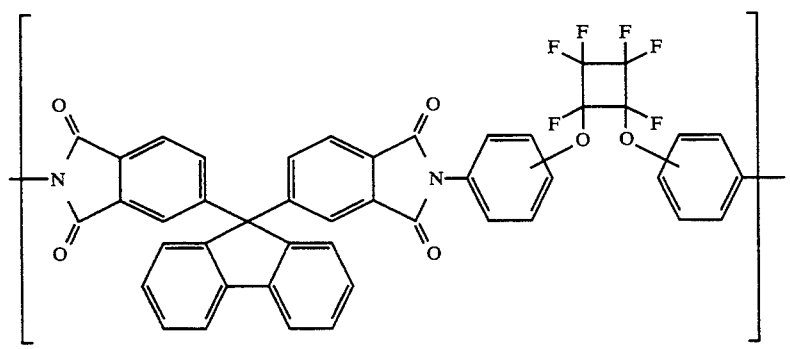
Formula VII
with meta or para substituted aniline-ether aromatic rings
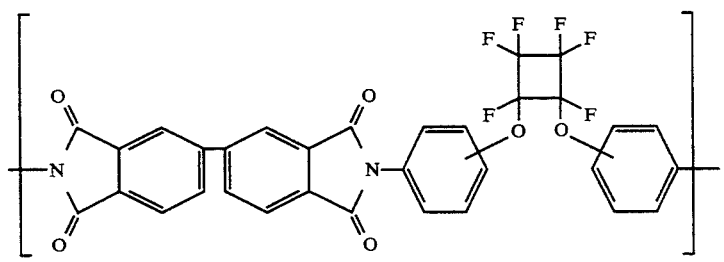
Formula VIII
with meta or para substituted aniline-ether aromatic rings
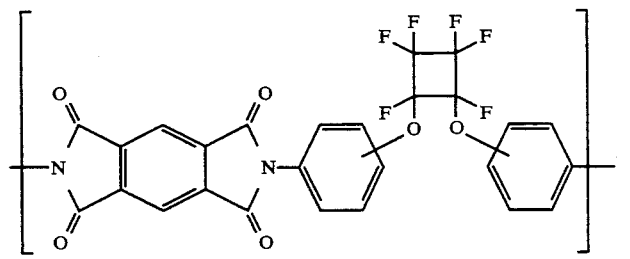
Formula IX
with meta or para substituted aniline-ether aromatic rings

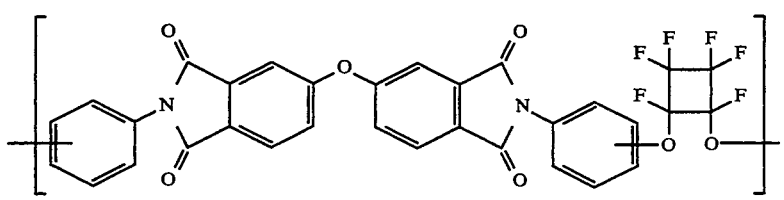
Formula X
with meta or para substituted aniline-ether aromatic rings
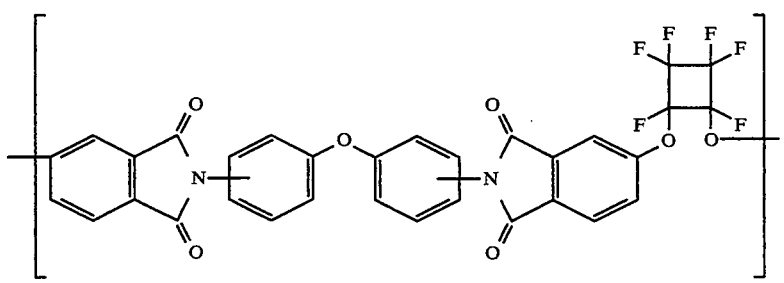
Formula XI
with meta or para substituted imide ethers.
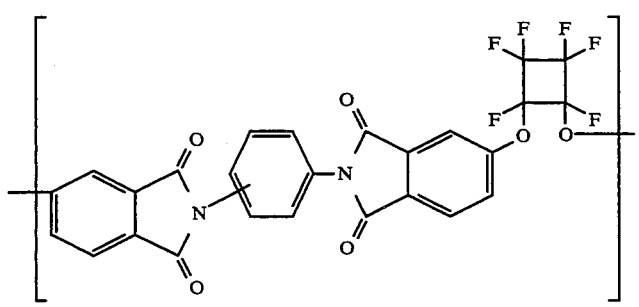
Formula XII
with meta or para substituted phenylenediamine aromatic rings
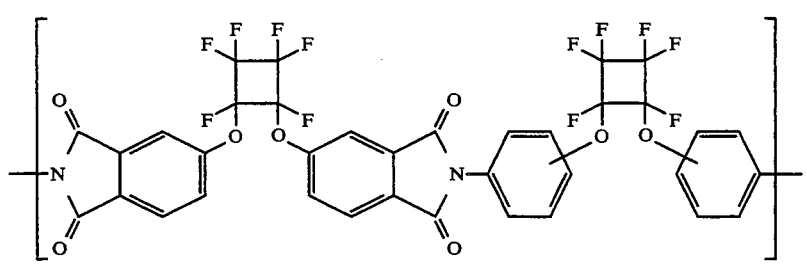
Formula XIII
with meta or para substituted aniline-ether aromatic rings
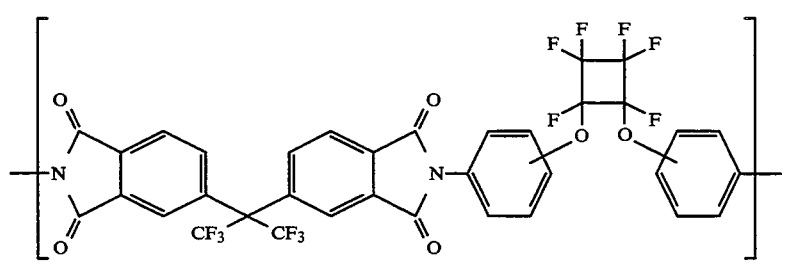
Formula XIV
with meta or para substituted aniline-ether aromatic rings

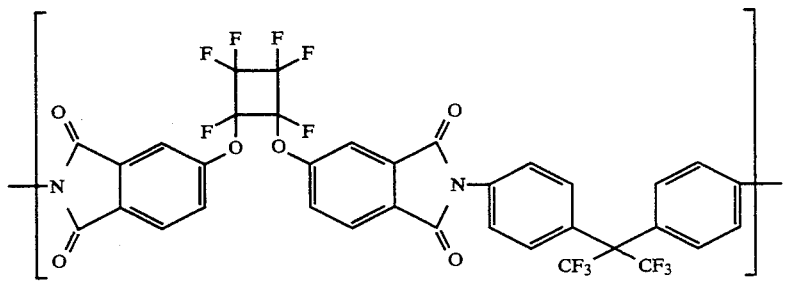
Formula XV
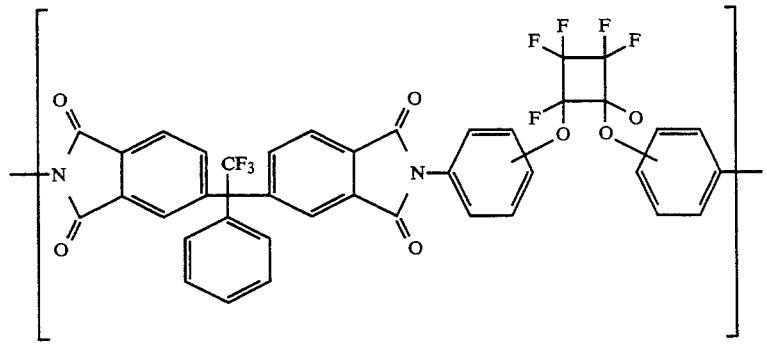
Formula XVI
with meta or para substituted aniline-ether aromatic rings
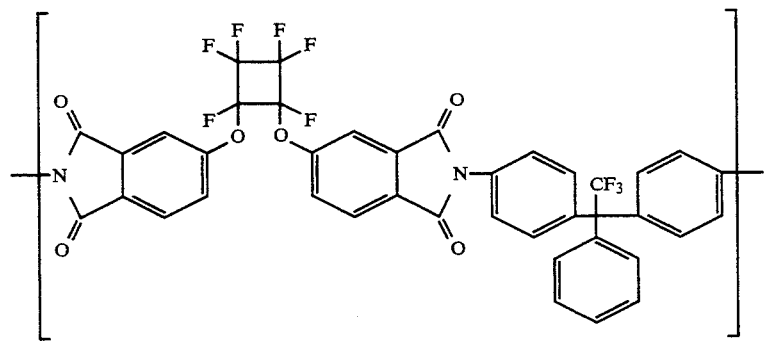
Formula XVII
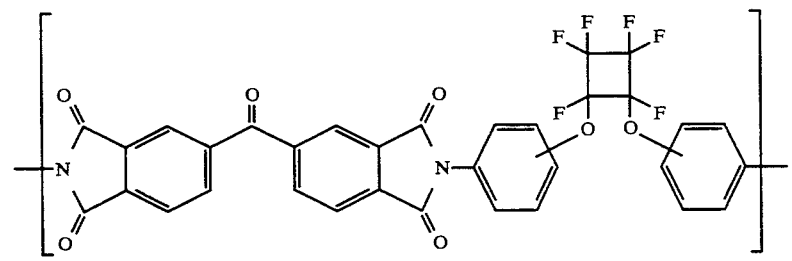
Formula XVIII
with meta or para substituted aniline ether rings
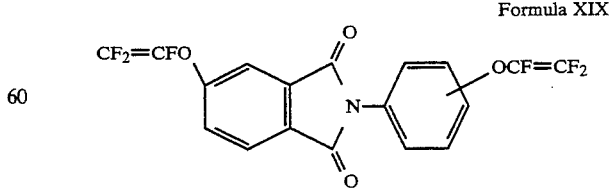
Formula XIX
wherein in each case Ar is as defined for Formula IVa. Additionally, monomers of the formula: are useful to prepare polymers having repeating units of the formulas:

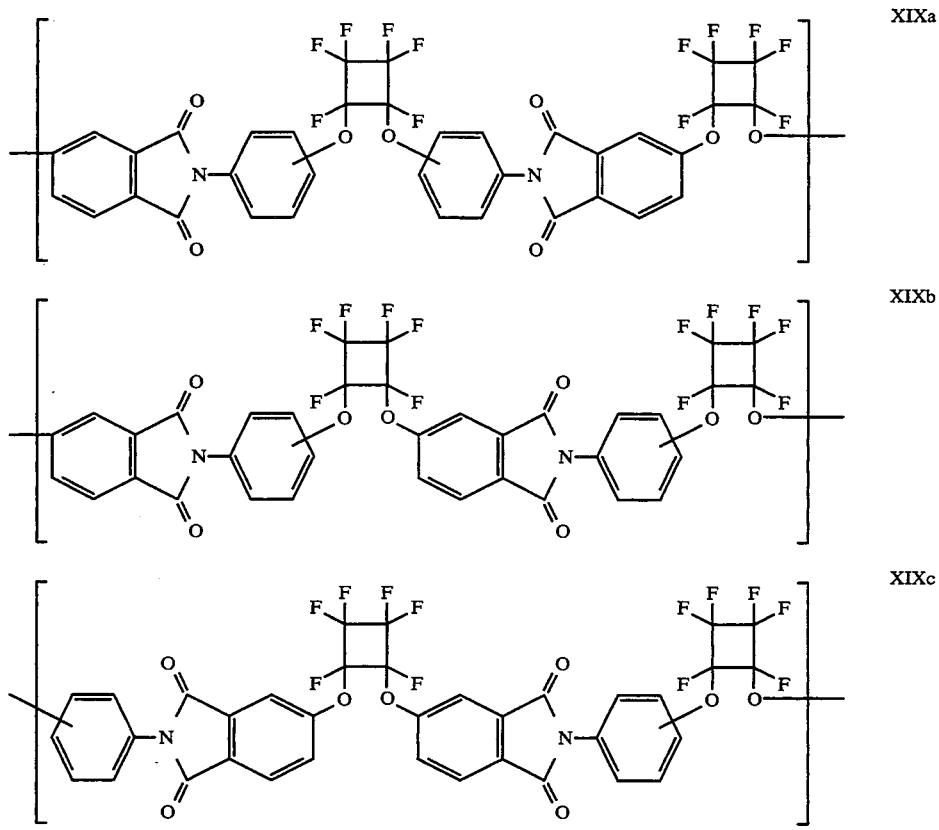

XIXa

XIXb

XIXc

XIX a,b, and c all with meta or para substituted aniline-ether aromatic rings.

Alternatively, perfluorocyclobutane groups are introduced into the polymer backbone by using a perfluorocyclobutane monomer with reactive functionality such as a dianhydride or diamine as described in Clement, et al. U.S. Pat. No. 5,021,602 in conjunction with compounds of the opposite functionality to form polyimides by means as described in "Polyimides-Synthesis, Characterization, and Applications" K. L. Mittal (ed.) Plenum Press 1984, Volume 1 and 2. For example a perfluorocyclobutane containing dianhydride such as 1,2-diphenoxyhexafluorocyclobutane-3′,3″,4′,4″-tetracarboxylic acid anhydride is reacted with a diamine such as 4,4′-oxydianiline to form a polyamic acid which is advantageously further reacted to form a polyimide by means within the skill in the art including both heat treatment and chemical imidization methods such as acid catalysis with azeotropic removal of water. Perfluorocyclobutane monomers with reactive functionality are also reacted with perfluorovinyl ether monomers to form perfluorovinyl ether terminated monomers or oligomers which contain perfluorocyclobutane groups in the backbone.

Another particularly useful embodiment of the present invention is the formation of linear, thermoplastic materials from monomers containing two trifluorovinyl groups. Generally monomers containing two vinyl groups result, by conventional addition polymerization, in highly crosslinked, brittle plastics. The present novel polymerization process is more akin to condensation polymerization in that difunctional monomers result in linear polymers. To obtain properties associated with structural plastics, it is preferred that R in Formula I is aromatic and most preferred that R contains more than one aromatic ring. It is also preferred that each X is oxygen or sulfur (optionally as sulfone or sulfoxide) and most preferably oxygen. The resulting aromatic perfluorocyclobutyl ether backbone in the thus formed polymers have exceptional physical properties combined with excellent melt processability on conventional thermoplastic fabrication equipment. A polymer exemplary of these characteristics is represented by Formula II wherein R is biphenyl, m is 1, and each X is oxygen. The monomer is conveniently prepared from 4,4′-dihydroxybiphenyl and dibromotetrafluoroethane by modification of chemistry described in U.S. Pat. No. 4,423,249 or by the process disclosed in copending U.S. Pat. No. 5,023,380 issued Jun. 11, 1991, which is incorporated herein in its entirety. The monomer is easily polymerized at a convenient rate by heating in bulk or solution at about 150° to about 200° C. Typical properties of a polymer prepared in perfluorotetradecahydrophenanthrene solvent are a glass transition temperature of about 170° C., tensile strength (as measured by the procedure of ASTM D-882-83) of from about 5000 to about 6000 psi (pounds per square inch), percent elongation (as measured by the procedure of ASTM D-882-83) of from about 10 percent to about 20 percent, tensile modulus (as measured by the procedure of ASTM D-882-83) of from about 200,000 to about 300,000, dielectric constant (as measured by the procedure of ASTM D150-87) of from about 2.45 to about 2.65, and static dissipation factor (as measured by the procedure of ASTM D150-87) of from about 0.0004 to about 0.0008.

Another preferred embodiment of the present process is to form linear perfluoropolymers, preferably having ether atoms incorporated in the polymer backbone. Polymers of this general class of compounds are generally prepared by fluoride ion catalyzed reactions of perfluorinated epoxides (U.S. Pat. Nos. 3,214,478 and 3,322,826). These type products having perfluorocyclic groups, including perfluorocyclobutane groups, are taught in U.S. Pat. No. 3,303,145. While the methods taught are suitable for preparing low weight average molecular weight materials, the method is generally unsuitable for producing higher weight average molecular weight products (e.g. weight average molecular weights of at least about 10,000). Elimination of fluoride to form acid fluoride terminal groups in the growing chains generally limits weight average molecular weight. This deficiency can be offset somewhat by lowering reaction temperature, but nevertheless the only commercially significant products produced using a process like that taught in the prior art patents are oligomeric fluids such as Krytox ® commercially available from I.E. DuPont and Company. Formation by the cyclopolymerization process of the invention makes possible production of higher weight average molecular weight polymers. Preferable perfluoro polymers of this embodiment of the present invention are thermally produced from monomers of Formula I wherein R is perfluoroalkyl, X is oxygen. These monomers are conveniently produced by known chemistry involving reaction of perfluoroalkyl compounds having two acid fluoride groups with fluoropropyl epoxides followed by decarboxylation to form vinyl ethers. (See U.S. Pat. No. 3,450,684 and 4,554,112). The resulting monomers, perfluoroalkyl dipedluorovinyl ethers, $CF_2=CFO(CFR_f)_nOCF=CF_2$, where $R_f$ is branched or linear fluoroalkyl (preferably of from about 1 to about 10 carbon atoms), or fluorine; and n is preferably between 1 and about 10, are then thermally polymerized to form polymers, or if desirable, oligomers having the repeating unit,

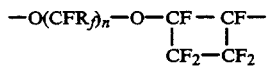

and terminated in trifluorovinyl ether groups. The polymers having weight average molecular weight above about 10,000, preferably above about 25,000 are useful in elastomer applications, particularly when cured by a crosslinking reagent. Suitable crosslinking reagents are monomers described herein where m is greater than 1. The terminal groups are conveniently further reacted, if desired, by a variety of processes within the skill in the art including radical initiated reactions or, alternately, are rendered inert by halogenation, preferably with fluorine. It is within the scope of the present invention to copolymerize the foregoing monomers, oligomers or polymers with other compounds of the present invention having two or more trifluorovinyl groups. For instance, oligomers of the divinylperfluoroethers are formed and cured with a perfluorovinyl compound, particularly of Formula I wherein R is aromatic, m is 2 and both X's are oxygen. This technique is useful for forming thermoset resins or elastomers depending on the proportion of multifunctional (m greater than 1) material used.

Polymers of the invention are suitably solids, fluids or gels, preferably solids or fluids, most preferably solids. The solids preferably maintain plastic characteristics such as tensile strength well above ambient temperatures (e.g. above about 25° C.) and have glass transition temperatures from well below ambient to well above ambient temperatures. A particularly preferred group of such polymers have glass transition temperatures (Tg) above ambient (25° C.), preferably above 60° C. and most preferably above 100° C. In general, the polymers having Tg above ambient result from monomers of Formula I wherein R is aromatic, and the polymers having Tg above 60° C. when R contains more than one aromatic ring. A particular desirable property of polymers where R is aromatic and not substituted with polar substituents (e.g. nitro, sulfonate, carboxy) is the combination of good physical properties and good electrical properties. Dielectric constants and static dissipation factors (as measured according to the procedures of ASTM D150-87) preferably range from about 2.2 to about 3.0 and from about 0.0002 to about 0.005 respectively. Glass transition temperatures increase from about ambient when R is phenyl to about 170° C. when R is biphenyl to 230° C. when R is 9,9-diphenylfluorene.

The linear polymers are advantageously thermoformed as by molding or extruding or are cast from solvents such as ethers and chlorinated solvents, for instance, tetrahydrofuran or dichloromethane. The polymers possess processing advantages over other polymers having similar low dielectric properties such as polytetrafluoroethylene. The advantages include extrudability, suitability for injection molding and solvent casting.

The following examples are offered to illustrate but not to limit the invention. In each case, percentages are weight percent unless otherwise indicated. Examples (Ex.) of the invention are indicated numerically, while comparative samples (C.S.) are not examples of the invention and are indicated with letters.

All gas chromatography/mass spectrometry (GC/MS) analyses of monomers and intermediates are performed on a Finnigan 1020 GC/MS using a 30 meter RSL-150 fused silica capillary column. All gas chromatography/mass spectrometry (GC/MS) analyses of fluid polymer samples are performed on a Finnigan 4500 GC/MS using a 60 meter DB-1 fused silica capillary column, with the GC program run at 290° C. isothermal. Liquid chromatography/mass spectrometry (LC/MS) is performed on a Finnigan 4500 mass spectrometer using acetonitrile- water eluent and a moving belt LC/MS interface.

Dynamic Mechanical Spectroscopy (DMS) measurements are performed on a Rheometrics RDS-7700 rheometer in torsional rectangular geometry mode using 60 mm×12 mm×3 mm samples at 0.05 percent strain and 1 Hz. Differential scanning calorimetry (DSC), thermomechanical analysis (TMA) and thermogravimetric analysis (TGA) is performed on a Perkin Elmer 7000 thermal analysis system.

Dielectric constant and dissipation factor measurements are conducted according to the procedures of ASTM D150-87. Tensile strength and modulus and percent elongation were measured on an Instron model 1125 according to the procedures of ASTM D-882-83.

Gel Permeation Chromatography (GPC) is performed on a Waters 720 GPC instrument using a methylene chloride eluent and a series of Micro-styrage ® columns of 10,000, 1,000, 500 and 100 angstrom pore sizes. Reported values are standardized against polystyrene.

Granular zinc is activated by washing in 0.1N hydrochloric acid (HCl) followed by drying in a vacuum oven at 0.5 torr and 140° C. for 10 hours.

Infrared (IR) spectra are measured on a Beckmann Microlab 600 model spectrophotometer. Nuclear Magnetic Resonance (NMR) spectra are measured on a Varian EM360 spectrometer using 19 F (fluorine 19) or 1H (hydrogen) mode.

EXAMPLE 1

Preparation and Bulk Polymerization of 4,4′-Bis(trifluorovinyloxy)biphenyl

Dimethyl sulfoxide (DMSO) (1800 ml)is placed in a 5-liter 5-necked flask fitted with a mechanical stirrer, a Dean-Stark phase separating trap topped with a nitrogen padded reflux condenser, and a thermocouple attached to a temperature controller. The solvent is stirred and purged of oxygen by blowing in nitrogen through a dip-tube placed below the surface of the liquid while 4,4′-dihydroxybiphenyl (454 g, 2.44 mole) is added to the flask.

The system is stirred and purged for 20 minutes, then potassium hydroxide (85 percent pellets) (322 g, 4.88 mole) is added slowly. The stirred mixture is then heated to 120° C. The temperature is held at 120° C. for 1.5 hours, then the heat is turned off and the mixture is allowed to cool to room temperature. Toluene (600 ml) which has been thoroughly purged with nitrogen is added to the solution and the resulting mixture is heated to reflux (135° C.). Water is azeotropically removed from the reactor through the Dean-Stark trap for a total of 4 days, cooling the reactor once after 24 hours to allow for salt formation to be broken up by opening the flask under a nitrogen sweep and scraping the sides with a spatula. After 4 days the Dean-Stark trap is removed and replaced with a Soxhlet extractor containing anhydrous sodium sulfate. The toluene is then refluxed through the Soxhlet extractor for 7 hours to dry the toluene. After 7 hours, the Soxhlet is replaced with a Dean-Stark trap, and toluene (300 ml) is removed from the reactor by simple distillation. The reaction mixture is then cooled to 30° C. in an ice water bath and 1,2-dibromotetrafluoroethane (1300 g, 5.00 mole) is added slowly dropwise over three hours at a rate that maintains a reactor temperature of 35±2° C. When the addition is complete the reaction temperature is allowed to stabilize (not increasing in temperature when the ice bath is removed) and then a heating mantle is applied to the flask. The reactor is heated to 50° C. for 8 hours, then allowed to cool to room temperature with constant stirring. The crude reaction mixture is filtered to remove the potassium bromide salts, and the precipitate is washed with acetone. The flitrates are combined and thoroughly evaporated to remove acetone, DMSO and residual toluene. The solid residue is subjected to a 2 liter Kugelrohr bulb-to-bulb distillation to provide the crude product. This material is dissolved in 750 ml of methylene chloride and is washed first with mild aqueous potassium bicarbonate (500 ml, approximately. 0.2M), then with mild aqueous hydrochloric acid (HCl) (500 ml, approximately 0.05M), then twice with distilled water (500 ml each). After complete phase separation the product layer is removed and evaporated, and the residue is fractionally distilled (138°14 148° C., 0.35 torr) to provide 1031.1 g (1.90 mole, 77.9 percent yield) of 4,4′-bis(2-bromotetrafluoroethoxy)biphenyl, melting point 71°–73° C. The Infrared (IR) spectra of the product has the following peaks (cm$^{-1}$): 1601,1492 (indicating an aromatic double bond); 1199–1107 (indicating carbon-oxygen and carbon fluorine bonds); 842, 788 (indicating aromatic character). The gas chromatograph/mass spectrometer (GC/MS) indicates peaks at the following mass to charge ratios (m/e)=545 (29.8 percent); 543 (48.9 percent); 541 (23.8 percent); 365 (48.7 percent); 363 (50.9 percent); 337 (30.3 percent); 335 (34.7 percent); 168 (33.7 percent); 156 (78.3 percent); 140 (36.7 percent); 139 (90.1 percent); 129 (37.4 percent); 128 (100.0 percent); 127 (33.2 percent); 102 (32.9 percent); 76 (41.1 percent); 63 (34.3 percent), consistent with a product of 4,4′-bis( 2-bromotetrafluoroethoxy)biphenyl.

Bromine is eliminated from this product by the following procedure:

Into a 1-liter 5-necked flask equipped with a mechanical stirrer, a thermocouple attached to a temperature controller, a powder addition funnel and a reflux condenser, is placed freshly distilled diglyme (200 ml) and fresh zinc powder (36.0 g, 0.55 mole).

The mixture is stirred and heated to 130° C. Powdered 4,4′-bis(2-bromotetrafluoroethoxy)biphenyl (100 g, 0.184 mole)is added very slowly via the powder addition funnel over 3.5 hours. The mixture is then stirred mechanically at 115° C. for 1 hour, after which heating is turned off and the mixture is allowed to cool to room temperature. The solution is centrifuged to remove the zinc salts. Then the liquid is decanted, and the zinc salts are washed with acetone and centrifuged again. The liquid portions are combined and evaporated thoroughly, and the residue is dissolved in methylene chloride and washed with 0.05M hydrochloric acid. The methylene chloride solution is evaporated to provide 62.45 g (0.180 mole) of 4,4′-bis(trifluorovinyloxy)-biphenyl of 94.5 percent purity in 98 percent yield.

The product is then recrystallized in an ethanol/water mixture to give product of 99.8 percent purity in greater than 70 percent recovery, melting point 44°–46° C.

The IR spectrum shows peaks at (cm$^1$): 1833 (indicative of a perfluorovinyl group); 1601,1491 (indicative of an aromatic double bond); 1231, 1196–1132 (indicative of carbon-oxygen and carbon-fluorine bonds respectively); 818 (indicative of aromaticity).

The GC/MS spectrum has the following peaks: m/e: 346 (31.3 percent); 153 (13.8 percent); 152 (100.0 percent); 151 (27.0 percent); 150 (11.7 percent); 76 (14.9 percent); 63 (14.9 percent).

Differential scanning calorimetry (DSC) analysis of the 4,4′-bis(trifluorovinyloxy)biphenyl monomer (20° C. to 360° C. at 20° C./minute) indicates a sharp endotherm of melting beginning at 45° C., followed by a broad exotherm beginning at about 170° C., interpreted as corresponding to the heat of cyclization of the trifluorovinyl groups to form hexafluorocyclobutane rings.

The monomer, 4,4′-bis(trifluorovinyloxy)bi-phenyl, (15.0 g, 0.043 mole) is placed in a nitrogen purged 100 ml round bottom flask and polymerized by heating at 210° C. for 2 hours without stirring. After cooling, a small sample is removed for analysis by differential scanning calorimetry (DSC). The sample shows a small crystalline melt with a peak at 60° C., followed by a broad exotherm beginning at about 200° C. The bulk sample is heated again at 235° C. for an additional 3 hours. Again a sample is removed and analyzed by DSC. The analysis indicates a very small crystalline melt with a peak at 60° C., followed by a low intensity exotherm beginning at about 230° C. The bulk sample is heated again to 265° C. for 45 minutes. Analysis of this sample indicates no crystalline melt and no exothermic activity up to and including 325° C., with the emergence of an endothermic glass transition (Tg) at 143° C.

Example 2

Polymerization of 4,4'-bis(trifluorovinyloxy)biphenyl in Solution

The monomer, 4,4'-bis(trifluorovinyloxy)bi-phenyl, (60.0 g, 0.173 mole) is placed in a 1 liter 3-necked round bottom flask with 75 ml of perfluorotetra-decahydrophenanthrene (Multifluor TM APF 215 commercially available from Air Products). The flask is fitted with a mechanical stirrer and a nitrogen padded reflux condenser. After purging the flask thoroughly with nitrogen, the mixture is stirred and heated to reflux. Initially, upon heating the melted monomer is not miscible with the solvent, but as the temperature rises the two phases become homogeneous. After stirring at reflux for approximately 45 minutes, a polymer phase separates; and, after stirring at reflux for a total of 3 hours, the phase separated polymer becomes viscous enough to seize the stirring shaft. The cooled polymer is removed from the flask and evaporated under high vacuum (approximately 0.50 torr) at about 220° C. for 3 hours to remove residual solvent. A portion of this polymer is compression molded at 250° C. to provide a light yellow, transparent flexible plastic film. Another portion is dissolved in tetrahydrofuran and placed in an evaporating dish to make a solvent-cast film. After the solvent is evaporated overnight, a light yellow thin film is peeled from the dish. This sample exhibits excellent flexibility and transparency.

An IR spectrograph of the film has the following peaks (cm$^{-1}$): 1601, 1490 (indicating aromatic double bonds); 1302, 1194-1115 (indicating carbon-oxygen and carbon-fluorine bonds), 818 (indicating aromaticity). DSC analysis of this polymer indicates a Tg transition at 148° C.

Dynamic mechanical analysis (DMS) gives a Tg value of 170°, and gel permeation chromatography (GPC) indicates a weight average molecular weight of 85,000 as standardized against polystyrene.

Dielectric constant and dissipation factor measurements performed on this polymer give the following results:

| Frequency (kHz) | Dielectric Constant | Dissipation Factor |
| --- | --- | --- |
| 1.0 | 2.58 | 0.0007 |
| 10.0 | 2.57 | 0.0004 |
| 1000.0 | 2.55 | 0.0004 |

Examples 1 and 2 illustrate two types of polymerization of 4,4'-bis(trifluorovinyloxy)biphenyl. It is notable that the properties of each are roughly similar, with slightly more discoloration taking place in the bulk polymerization (according to the procedures of Example 1).

Example 3

Preparation and Polymerization of 9,9-bis(4'-[trifluorovinyloxy]phenyl)fluorene

Into a 2 liter 5-necked round bottom flask fitted with a mechanical stirrer, Dean-Stark trap topped with a nitrogen padded reflux condenser and a thermocouple attached to a temperature controller, are placed DMSO (650 ml) and toluene (200 ml). While the stirred solution is purged with nitrogen, 9,9-bis(4'-hydroxyphenyl)fluorene (200.0g, 0.57 mole) is added to the flask. While purging with nitrogen continues, potassium hydroxide (85 percent pellets, 77.5 g, 1.17 mole) is added all at once, and the mixture is heated to 100° C. with constant stirring. After two hours, the temperature is increased until the solution begins to reflux (130° C.). Water is removed by azeotropic distillation for 24 hours. The Dean-Stark trap is replaced by a Soxhlet extractor containing anhydrous sodium sulfate, and the toluene is refluxed through the Soxhlet for 5 hours. A small amount of toluene (60 ml) is then removed by simple distillation. Then the reactor is cooled to 35° C. Addition of 1,2-dibromotetrafluoroethane (315 g, 1.21 mole) via dropping addition funnel is then maintained at a rate that keeps the reaction temperature at 35°-38° C. When the addition is complete, the mixture is heated at 50° C. for 8 hours, then cooled to room temperature with constant stirring. The mixture is filtered, and the precipitate is washed twice with acetone. The flitrates are combined and evaporated thoroughly. The residue from the evaporation is washed with water to remove residual potassium bromide (KBr). After the residue is air dried for 24 hours, it is extracted with hexane in a Soxhlet extractor. Evaporation of the hexane, followed by column chromatography of the residue (on neutral alumina, using hexane eluent) provides a product, 9,9-bis(4'-[2''-bromotetrafluoroethoxy]phenyl)fluorene (331.4 g, 0.468 mole, 82 percent yield), melting point 157°-158° C.

The LC/MS spectrum has peaks at: m/e: 710 (53.0 percent); 709 (34.0 percent); 708 (100.0 percent); 707 (23.3 percent); 706 (49.8 percent); 513 (28.4 percent); 511 (28.5 percent); 438 (12.8 percent); 437 (52.4 percent); 436 (14.7 percent); 435 (55.8 percent); 355 (15.7 percent); 290 (33.9) percent; 289 (19.5 percent); 239 (35.9 percent); 228 (36.2 percent); 227 (38.9 percent); 226 (47.3 percent); 202 (27.7 percent); 157 (47.2 percent); 131 (27.6 percent); 129 (23.1 percent).

The product from the above reaction (18.85 g, 0.027 mole) is combined with freshly activated granular zinc (5.00 g, 0.076 mole) in glyme and heated at reflux overnight. After cooling, the reaction mixture is decanted and centrifuged to remove suspended zinc salts. The solvent is removed by vacuum evaporation, and the residue is purified by column chromatography on neutral alumina using hexane as an eluent to provide as product 9,9-bis(4'-trifluorovinyloxyphenyl)fluorene (5.55 g, 0.011 mole, 40 percent yield), melting point 115°-116° C.

The LC/MS spectrum has peaks at: m/e: 511 (29.3 percent); 510 (91.9 percent); 337 (37.2 percent); 316 (16.1 percent); 315 (19.7 percent); 313 (12.8 percent); 241 (15.5 percent); 240 (52.8 percent); 239 (100.0 percent); 237 (15.6 percent); 207 (14.1 percent); 158 (28.7 percent); 157 (53.1 percent); 155 (14.4 percent); 150 (28.8 percent); 145 (18.3 percent); 144 (16.5 percent); 120 (15.1 percent).

Into a 50 ml round bottom flask fitted with a nitrogen padded reflux condenser, mechanical stirrer and a thermocouple attached to a temperature controller are placed 9,9-bis(4'-trifluorovinyloxyphenyl)fluorene (3.0 g, 0.0059 mole) and diphenyloxide (5.0 ml). The mixture is stirred and heated to reflux (255° C.) for 22 hours. The diphenyloxide (DPO) solvent is evaporated under high vacuum on a 100 milliliter Kugelrohr bulb to bulb apparatus (0.03 mm, 165° C.) to provide the polymer product, which is dissolved in methylene chloride and cast into a thin film.

Gel permeation chromatography analysis of the polymer indicates a weight average molecular weight of 135,000 as standardized against polystyrene.

DSC analysis indicates a Tg transition at 224° C.

Example 3 illustrates preparation and polymerization of of 9,9-bis(4,4'-trifluorovinyloxyphenyl)fluorene. It is notable that the resulting polymer, which is polymerized in DPO, attains a high weight average molecular weight and forms a solvent cast film with good physical properties such as flexibility.

Examples 4–9

Preparation and Polymerization of a variety of Perfluorocyclobutane Ring-Containing Polymers The procedure outlined in Example 3 is repeated for each of the indicated starting materials, except for the changes indicates in Table I and adjustments in amounts to maintain the stoichiometry of Example 3, to produce the indicated monomers of the structure:

$$CF_2=CF-O-R-O-CF=CF_2$$

wherein R is given in Table 1.

TABLE 1

| Ex. No. | Starting Material | R | Changes In Procedure |
|---|---|---|---|
| 4 | Resorcinol | 1,3-Phenylene | Tetraglyme is used in second step. Product is distilled directly from reaction mixture under vacuum. *3-(1',1',2',2'-tetrafluoroethoxy)-trifluorovinyloxy benzene and 1,3-bisphenol (1',1',2',2'-tetrafluoro-ethoxy)trifluorovinyloxybenzene are isolated as by products and identified by GC/MS spectra consistent with those compounds. |
| 5 | 4,4'-dihydroxybiphenyl | 4,4'-Biphenyl | See Example 1 |
| 6 | 4,4'-thiodiphenol | 4,4'-Thiodiphenyl | Tetraglyme is used in second step, removed by diluting with methylene chloride and washing with water. |
| 7 | Bisphenol A | Isopropyl-2,2-diphenylene | |
| 8 | Hexafluorobisphenol A (bisphenol AF) | Hexafluoro-isopropy 1-2,2-diphenylene | |
| 9 | 9,9-bis (4'-hydroxyphenyl) fluorene | 9,9-bis (4'-phenylene) fluorene | See Example 3 |

The data in Table I shows that a variety of perfluorovinyl monomers are prepared by processes within the scope of the invention.

The procedure outlined in Example 2 is repeated for each of the monomers in Table I, except for the changes in procedure indicated in Table II to produce polymers from the indicated monomers. The properties of these polymers are given in Table II.

TABLE II

| | | | Properties of Thermoplastic Polymers | | |
|---|---|---|---|---|---|
| Ex. | R | Tg (°C.) | Dielectric Constant 10 kHz | Dissipation Factor 10 kHz | Wt. Ave. Molecular weight |
| 4 | 1,3-Phenylene | 32° | 2.41 | — | 41,400 |
| 5 | 4,4'-Biphenyl | 170° | 2.57 | 0.0004 | 85,000 |
| 6 | 4,4'-Thiodiphenyl | 78° | 2.62 | 0.0005 | 42,500 |
| 7 | Isopropyl-2,2-diphenylene | 98° | — | — | 50,700 |
| 8 | Hexafluoro-iso-propyl-2,2-diphenylene | 125° | — | — | 23,500 |
| 9 | 9,9-bis(4'-phenylene)fluorene (prepared in diphenyl-oxide) | 224° | — | — | 135,000 |

The data in Table II shows that a variety of perfluorocyclobutane ring-containing polymers are prepared by processes within the scope of the invention.

Example 10

Preparation of 1,1,1-TRIS(4'-trifluorovinyloxyphenyl)ethane and Bulk Polymerization thereof with 4,4'bis(trifluorovinyloxy) biphenyl A 1 liter 5-necked round bottom flask is fitted with a mechanical stirrer, a Dean Stark trap topped with a nitrogen padded reflux condenser, and a thermocouple attached to a temperature controller. A mixture of DMSO (450 ml), toluene ( 150 ml), and 1,1,1 -tris(4'-hydroxyphenyl)ethane (55.1 g, 0.18 mole) is added to the flask under nitrogen purge. After stirring for 15 minutes under a vigorous nitrogen purge, potassium hydroxide (85 percent pellets, 80.Og, 1.2 mole) is slowly added to the reaction flask. The mixture is then stirred at reflux for 48 hours with azeotropic removal of water. The resulting suspension is cooled to 35° C. in an ice bath and 1,2-dibromotetrafluoroethane (155 g, 0.60 mole) is added at a rate that maintains a temperature of 30°–35° C. When the addition is complete, the mixture is heated to 50° C. with continuous stirring for 3 hours. After filtration, the solvents are removed by heating under vacuum on a rotary evaporator. The brown residue is purified by column chromatography on neutral alumina using hexane as eluent to provide as product 1,1,1-tris(4'-[2'''-bromotetrafluoroethoxy]phenyl)ethane ( 18.3 g, 0.022 mole, 12 percent yield).

Identity of the product is confirmed by a GC/MS spectrum, the following peaks: m/e: parent ions m/e 840-842-844-846 (ratio 1:3:3:1 ) too heavy to detect. Structure determined from fragmentation: 573 (32.3 percent); 571 (58.3 percent); 569 (31.5 percent) [indicating parent - $PhOCF_2CF_2Br$]). 299 (58.1 percent); 297 (52.7 percent); 279 (32.3 percent); 228 (43.5 percent); 227 (31.5 percent); 226 (36.0 percent); 215 (59.5 percent); 181 (82.1 percent); 179 (100.0 percent); 165 (50.3 percent); 152 (43.7 percent); 131 (47.1 percent); 129 (50.4 percent); 100 (38.8 percent).

Into a 500 ml 5-necked flask fitted with a mechanical stirrer, a reflux condenser, and a thermocouple attached to a temperature controller is placed freshly activated granular zinc (4.3 g, 0.066 mole) and 25 ml dry diglyme. This mixture is stirred and heated to 110° C. under nitrogen while the product from the above reaction (18.0 g, 0.021 mole) is dissolved in 21 ml diglyme and added dropwise. The resulting mixture is stirred at 115° C. for 3 hours, then cooled and filtered. The flitrate is evaporated at 60° C. under vacuum to remove the diglyme, and the residue is purified by column chromatography on neutral alumina using hexane as eluent to provide the product 1,1,1-tris(4'-trifluorovinyloxyphenyl)ethane (9.98 g, 0.018 mole, 87 percent yield).

The GC/MS spectrum has the following peaks: m/e: 546 (3.2 percent); 531 (44.0 percent); 434 (17.9 percent); 373 (24.4 percent); 276 (16.9 percent); 240 (28.1 percent); 239 (73.9 percent); 199 ( 19.3 percent); 178 ( 100.0 percent); 177 (17.8 percent); 176 (25.4 percent); 163 (17.3 percent); 152 (31.9 percent); 151 (17.8 percent); 127 (20.3 percent); 126 (28.7 percent); 120 (39.1 percent); 119 (70.3 percent); 118 (25.6 percent); 113 (27.3 percent); 107 (18.8 percent); 102 (31.7 percent); 77 (15.9 percent); 76 (29.5 percent).

This example illustrates preparation of a trifunctional monomer, 1,1,1-tris(4'-trifluorovinyloxyphenyl)ethane. This monomer is useful alone or mixed with a bifunctional monomer to produce a crosslinked perfluorocyclobutane polymer.

A mixture of 4,4'-bis(trifluorovinyloxy)biphenyl (as prepared in Example 1) (4.50 g, 0.013 mole) and the 1,1,1-tris(4'-trifluorovinyloxyphenyl)ethane (0.79 g, 0.0014 mole) are combined in a 100 ml single necked round bottomed flask topped with a nitrogen padded reflux condenser. The flask is purged thoroughly with nitrogen, and the mixture is heated without stirring. After reaching a temperature of 200° C., the mixture sets into a rigid plastic within 15 minutes. This material is then cured an additional 40 minutes at 220° C.; then the heat is removed. The resulting plastic is rigid, inflexible and does not dissolve in tetrahydrofuran (THF) or methylene chloride, but swells into a gel in these solvents.

DSC analysis (25°-350° C., 20° C./min.) of this polymer sample shows a slight endothermic event at 125° C. followed by a broad exotherm beginning at about 210° C., indicative of an incompletely cured polymer. After this sample is cured during the first DSC scan, a second scan is run which clearly indicates a Tg transition at 151 ° C. and no subsequent exothermic activity at higher temperatures.

Example 10 illustrates preparation of 1,1,1-tris(4'-trifluorovinyloxyphenyl)ethane and copolymerization thereof 4,4'-bis(trifluorovinyloxy)biphenyl therewith. The resulting polymer is stiff and brittle, as well as insoluble, compared to the thermoplastic of Example 2, prepared from 4,4'-bis(trifluorovinyloxy)biphenyl alone, which is flexible and soluble in THF and methylene chloride.

Example 11

Bulk Polymerization of 4,4'-bis(trifluorovinyloxy)biphenyl with Subsequent Addition of 1,1,1-TRIS(4'-trifluorovinyloxyphenyl)ethane Monomer 4,4'-bis(trifluorovinyloxy)biphenyl(16.2 g, 0.047 mole) is placed in a 500 ml round bottom flask along with a magnetic stirring bar. A nitrogen padded reflux condenser is placed on the flask, and the monomer is heated at 200°-205° C. with stirring for 20 minutes, to form a low weight average molecular weight polymer resembling a thick fluid at 200° C. The fluid is allowed to cool to room temperature where it sets into a brittle glass. The glass is dissolved in methylene chloride and 1,1,1-tris(4'-trifluorovinyloxyphenyl) ethane (0.5 1 g, 0.00094 mole) is added to the solution. The methylene chloride is evaporated and the residue is dried and devolatilized on a Kugelrohr bulb to bulb apparatus at 120°-140° C. and 0.20 torr pressure. While still hot, the fluid mixture is poured into a mold and cured on a hot press at 250° C. and 20,000 psi for one hour. The mold is removed from the press and cooled. A coupon is removed from the mold. The coupon is a strong and flexible plastic, and does not dissolve in THF but swells into a gel therein.

DSC analysis of this crosslinked polymer sample indicates a Tg value of 149° C., with no subsequent thermal activity up to and including 350° C.

Example 11 illustrates polymerization of 4,4'-bis(trifluorovinyloxy)biphenyl with subsequent addition of 1,1,1-tris(4'-trifluorovinyloxyphenyl)ethane. It is notable that crosslinked polymers are prepared either by copolymerizing difunctional and multi-functional monomers, as in Example 10, or by combining a multifunctional monomer with a low weight average molecular weight polymer containing trifluorovinyl end groups as in Example 11.

Example 12

Preparation of 1,4-bis(trifluorovinyl)benzene and Bulk Polymerization Thereof

A 5 liter 3-necked round bottom flask is fitted with a mechanical stirrer, a nitrogen padded reflux condenser and a rubber septum. Glyme (100 ml) and activated zinc granules (11.50 g, 0.18 mole) are added to the flask along with a magnetic stirring bar. The flask is then purged with nitrogen for 15 minutes, after which time iodotrifluoroethylene (20.3 g, 0.098 mole) is added slowly via syringe through the septum. After 20 minutes of stirring the mixture begins to turn brown and get warm. After 2 hours a white precipitate begins to form. After stirring is continued without heat for 4 hours, the flask is opened under a slow nitrogen purge and 1,4-diiodobenzene (16.0 g, 0.0485 mole) is added along with palladium tetrakis(triphenylphosphine) (0.57 g, 0.00049 mole). The mixture is stirred overnight, resulting in the formation of a large amount of suspended solid. The reaction is allowed to stir an additional 24 hours, after which it is filtered, and the precipitate is washed with hexane (3 times with 50 ml each wash). The filtrates are combined and evaporated at 30° C. on a rotary evaporator to provide a residue which is purified by column chromatography (neutral alumnia, hexane eluent) to give 7.50 g of $CF_2=CF-Ph-CF=CF_2$ as product (0.0315 mole, 65 percent yield). This product is analysed by GC/MS and gives the following spectrum: m/e: 238 (100 percent); 188 (12.0 percent); 187 (46.4 percent); 169 (92.0 percent); 138 (18.8 percent); 99 (16.3 percent); 81 (12.3 percent); 69 (30.1 percent). The material is found to be air sensitive, fuming acid gasses if left exposed to oxygen.

This example illustrates preparation of an aromatic monomer having two perfluorovinyl groups directly attached to the aromatic ring and illustrate the use of iodotrifluoroethylene in preparation of a monomer. This preparation proceeds via a one pot synthesis to give good yields of the monomer.

It is noted that when a sample of this material is stored for 10 hours or more in contact with air that a highly mobile gel is formed along with the evolution of acid fumes. This observation is believed to be indicative of formation of acyl fluorides and fluoride ions, and of addition polymerization (rather than cyclization) catalyzed by the fluoride ion. The result of such storage in contact with air differs from the following product in that only a very low weight average molecular weight gel is formed, with a high degree of crosslinking taking place in the gel matrix.

Monomer 1,4-bis(trifluorovinyl)benzene (1.00 g, 0.0042 mole) is placed in a 100 ml round bottom flask with a magnetic stir bar and purged with nitrogen. The neat monomer is heated to about 80° C. with slow stirring. In 10 minutes the monomer sets into a hard glassy polymer which is not soluble in THF or methylene chloride, but which turns brown and fumes acid gasses when left exposed to air overnight. This observation suggests that a low weight average molecular weight polymer is formed and contains unreacted trifluorovinyl groups which are still air sensitive.

Example 12 illustrates polymerization of an aromatic monomer having two perfluorovinyl groups directly attached to the aromatic ring, which polymerization proceeds in a very short time and without the need of solvents.

Example 13

Solution Polymerization of 1,4-bis(trifluorovinyl)benzene

Monomer 1,4-bis(trifluorovinyl)benzene (1.00 g, 0.0042 mole) is combined in a 100 ml round bottom flask with 2.0 g of perfluorotetradecahydrophenanthrene (Multifluor ®) APF-215 commercially available from Air Products) and a magnetic stirrer. The flask is topped with a nitrogen padded reflux condenser. When the mixture is purged with nitrogen, it is heated to reflux with stirring. After 10 minutes, a crystalline precipitate is formed. This precipitate is isolated by filtration followed by vacuum drying.

The material is insoluble in THF or methylene chloride. A powder is formed by crushing the polymer precipitate in a mortar and pestle. Analysis of the powder by DSC indicates two small exothermic events, one at 180°–240° C., the other at 320°–380° C. leading into decomposition.

Example 13 illustrates solution polymerization of an aromatic monomer having two perfluorovinyl groups directly attached to the aromatic ring. This polymerization proceeds very quickly at higher temperatures and in the presence of inert solvents such as that used above.

Example 14

Preparation and Polymerization of 4,4'-bis(trifluorovinyl)biphenyl

A 1 liter 5-necked round bottom flask is fitted with a mechanical stirrer, a nitrogen padded reflux condenser and a rubber septum. Dry glyme (300 ml) and activated zinc granules (50.8 g, 0,395 mole) are added to the flask as it is purged thoroughly with nitrogen. Then iodotrifluoroethylene (100.0 g, 0.48 mole) is added to the flask all at once, and the mixture is stirred continuously under nitrogen for 5 hours. 4,4'-Diiodobiphenyl (97.0 g, 0.24 mole) is added to the flask along with nitrogen purged dimethylformamide (DMF) (300 ml) and palladium tetrakis(triphenylphosphine) (4.35 g, 0.0038 mole). The mixture is stirred at room temperature.

After 24 hours, a GC/MS of the mixture allows identification of all the reaction components. After 72 hours, the reaction seems to stop proceeding while excess diiodobiphenyl remains; another batch of iodotrifluoroethylene (25.0 g, 0.12 mole) is reacted with zinc in THF and added to the reaction mixture along with 1.0 g of palladium tetrakis(triphenylphosphine) catalyst. The reaction is allowed to stir an additional 12 hours, then is removed and evaporated to dryness under high vacuum on a rotary evaporator. Residue from evaporation is added to a 3 fold volumetric excess of water. A heavy precipitate is formed which is filtered and air dried on a vacuum funnel. The precipitate is dissolved in THF and filtered. Resulting flitrate is coated on silica gel by adding the silica gel to the THF solution and evaporating to dryness. This silica gel is then eluted on a short silica gel column using hexane as eluent to remove the colored material from the product. A fine white crystalline material remains after evaporation of the hexane. This crystalline material is then chromatographed again carefully on an alumina column using hexane as an eluent. The first band to elute from the column is the desired monomer product $CF_2=CF-Ph-Ph-CF=CF_2$. A total of 44.2 g of product is recovered (58.7 percent yield).

The crystalline product has a melting point of 83°–84.5° C.

Analysis by GC/MS gives the following mass spectral data for this product: m/e: 314 (100.0 percent); 263 (13.4 percent); 243 (14.9 percent); 69 (13.0 percent).

DSC analysis of this monomer shows a sharp endotherm at about 82° C. followed closely by a broad exotherm corresponding to cyclization of the trifluorovinyl groups beginning at about 98° C. A second exothermic event begins at about 300° C. leading into decomposition at >400° C. The monomer is also oxidatively unstable, as indicated by turning brown and releasing acid fumes when allowed to stand in air.

Example 14 illustrates preparation of another aromatic monomer having two perfluorovinyl groups directly attached to the aromatic ring. Because of the crystalline nature of this product, a gel is not formed on standing, although oxidative decomposition does appear to evolve acid gasses at a somewhat slower rate than the product of Example 12.

A sample of the 4,4'-bis(trifluorovinyl)bi-phenyl(1.6 g, 0.005 mole) and fresh anhydrous DMF (5.0 ml) are added to a 100 ml single necked round bottom flask with a thermometer port along with a magnetic stirrer. The flask is topped with a nitrogen padded reflux condenser and stirring is begun as nitrogen is allowed to pass out of the thermometer port. After 5 minutes of nitrogen purge, a thermocouple is placed in the thermometer port and heating is begun. The solution is heated to 40° C. for 4 hours with no apparent reaction. The temperature is then raised in 10° C. increments, holding each new temperature for at least 45 minutes before proceeding to the next higher temperature. After the mixture is stirred at 130° C. for 2 hours with no apparent change, the temperature is raised to 135° C. and left to stir overnight. The next morning the mixture is somewhat darker and noticeably higher in viscosity. The temperature is then raised to 140° C. for 9 hours, after which the mixture becomes very thick, at which time heating and stirring are stopped. A sample of the viscous liquid is removed and evaporated to dryness under vacuum, leaving a brittle crystalline powder. This powder dissolves in methylene chloride but does not filter through a 5 micron filter. Only a few drops of flitrate are recovered, and this flitrate is analyzed by gel permeation chromatography as standardized against polystyrene. As recovered by this method, the soluble portion of the polymer has a weight average molecular weight of 41,600.

DSC analysis of the crystalline polymer shows no thermal activity up to and including 400° C., with apparent decomposition beginning at about 420° C. All of the polymer samples prepared from this monomer are still air sensitive, as is evidenced by fuming of acid gasses after standing in air.

Example 14 illustrates polymerization of an aromatic monomer having two perfluorovinyl groups directly attached to the aromatic ring. This example also illustrates that careful temperature control may be employed to control the rate and extent of polymerization.

Example 15

Preparation of a Fluid Polymer of
1,3-bis(trifluorovinyloxy)benzene and
3-trifluorovinyloxy -1', 1', 1'-trifluorotoluene To synthesize m-trifluorovinyloxy-1', 1', 1'-trifluorotoluene, DMSO (400 ml), toluene (140 ml), and 3-trifluoromethylphenol (81.0 g, 0.50 mole) are placed in a 1 liter 3-necked flask equipped with a mechanical stirrer, a Dean-Stark trap and a thermocouple attached to a temperature controller. The stirred solution is purged of oxygen by placing a dip tube below the surface of the solution and allowing nitrogen to be blown into the solution for 15 minutes. Potassium hydroxide (85 percent pellets, 33.7 g, 0.51 mole) is added to the flask all at once, and a line to supply nitrogen is attached to a reflux condenser which is placed on top of the Dean-Stark trap. The mixture is then heated to 145° C. and water is removed azeotropically. When water ceases to collect in the Dean-Stark trap, the temperature of the reaction is increased to 155° C. and 100 ml of toluene is removed by distillation, leaving a reaction mixture in the flask.

The reaction mixture is cooled to room temperature, and 1,2-dibromotetrafluoroethane (132.0 g, 0.51 mole) is added slowly using a dropping addition funnel. The mixture is heated to 55° C. for 5 hours, then allowed to cool to room temperature. After the suspended solids have settled, the liquid is decanted away from the precipitate and is retained as a mixture of product in DMSO, which is added to a 3 times volumetric excess of water in a separatory funnel and shaken vigorously. The product forms a separate, lower layer at the bottom of the funnel and is removed. This crude product (lower layer) is washed again with 500 ml of water. After drying the washed lower layer over anhydrous magnesium sulfate, the crude product is fractionally distilled. The product, m-(2-bromotetrafluoroethoxy)- 1', 1', 1'-trifluorotoluene (169°–171° C., 150 torr) gives the following mass spectral data: m/e: 342 (20.1 percent); 340 (19.8 percent); 323 (7.9 percent); 321 (7.2 percent); 211 (25.6 percent); 145 (100.0 percent).

The product of the above reaction (56.0 g, 0.164 mole) is combined with granular zinc (12.0 g, 0.18 mole) in dry tetraglyme and stirred at 115° C. for 6 hours to form a reaction mixture. The mixture is cooled to room temperature, and a distillation head is placed on the reaction flask. The product is then distilled directly out of the crude reaction mixture (108°–110° C., 150 torr) to give 40.5 g of the product, m-trifluorovinyloxy- 1', 1', 1'-trifluorotoluene, which is 78 percent pure by GC analysis, with the remainder of the product being the by-product m-( 1,1,2,2,-tetrafluoroethoxy)-1', 1', 1'-trifluorotoluene.

The product gives the following mass spectral data: m/e: 242 (52.3 percent); 223 (12.3 percent); 195 (14.2 percent); 145 (100 percent); 125 (18.3 percent); 95 (30.6 percent).

A mixture is prepared from 1.25 ml of 1,3-bis(trifluorovinyloxy)benzene (as prepared in Example 4) and 8.75 ml of 3-trifluorovinyloxy-1',1', 1'-trifluorotoluene to make a total of 10 ml. This mixture is placed in a 50 ml round bottom flask fitted with a nitrogen padded reflux condenser and is refluxed under nitrogen for 20 hours.

The resulting product is analyzed by GC/MS and found to be a mixture of hexafluorocyclobutane products whose major components are 1,2-bis(3'-trifluoromethylphenoxy) hexafluorocyclobutane and 1,3-bis(2'-[3''-trifluoromethylphenoxy]hexafluorocyclobutyl)phenyl ether (having two perfluorocyclobutane rings), with a trace amount of 1,2-bis(3'-[2''-{3'''-trifluoromethylphenoxy}hexafluorocyclobutyloxy]-phenyl) hexafluorocyclobutyl ether (having three perfluorocyclobutane rings). By vacuum distillation two fractions are collected.

The first fraction contains primarily mono-perfluorocyclobutane material consisting of two isomers (cis and trans 1,2-substituted hexafluorocyclobutane) with similar mass spectra (given for one isomer only): m/e: 484 (20.2 percent); 465 (12.9 percent); 273 (29.2 percent); 242 (30.1 percent); 207 (11.2 percent); 195 ( 13.0 percent); 145 ( 100.0 percent);

The second fraction contains predominantly di-perfluorocyclobutane material, consisting mainly of three isomers (cis-cis, cis-trans, and trans-trans) of 1,2-substituted hexafluorocyclobutanes, and small amounts of four isomers of a product containing one 1,2-substituted hexafluorocyclobutane ring and one 1,3-substituted hexafluorocyclobutane ring (cis- 1,2 cis- 1,3; cis- 1,2 trans- 1,3; trans-1,2 cis-1,3; and trans-1,2 trans-1,3). All seven products give roughly the same peaks in their mass spectra in differing intensities. The following mass spectral data is for the first product isomer to elute from the gas chromatography (GC) column, and corresponds to one of the three main isomers of two perfluorocyclobutane rings: m/e: 754 (36.4 percent); 593 (12.5 percent); 492 (14.1 percent); 415 (21.9 percent); 273 (27.7 percent); 242 (39.1 percent); 195 (21.5 percent); 173 (23.4 percent); 145 (100.0 percent); 126 (28.5 percent); 95 (23.1 percent); 92 (34.7 percent); 76 (57.6 percent); 64 (27.3 percent).

The second fraction also contains a small amount of material containing three perfluorocyclobutane rings, consisting of six isomers (cis-cis-cis, cis-cis-trans, cis-trans-cis, cis-trans-trans, trans-cis-trans, and trans-trans-trans) of 1,2-substituted hexafluorocyclobutanes. Because of the small amount of this product present in the mixture, the corresponding products containing one or more 1,3-substituted hexafluorocyclobutane rings are not detected. The mass spectra of the six isomers showed roughly the same peaks in slightly differing intensities. The following mass spectral data is from the first product isomer of tri-perfluorocyclobutane material to elute from the GC column: m/e: 1024 (21.6 percent); 593 (16.3 percent); 492 (35.5 percent); 415 (17.6 percent); 281 (16.2 percent); 273 (16.4 percent); 242 (26.0 percent); 208 (15.9 percent); 207 (71.9 percent); 145 (100.0 percent); 92 (19.7 percent); 76 (26.8 percent).

In all cases, the primary products of cyclization are 1,2-substituted hexafluorocyclobutanes, with small amounts (1–2 percent) of 1,3-substituted hexafluorocyclobutanes observable by GC/MS, (except for the triperfluorocyclobutane material, of which only trace amounts are seen) the two being distinguished by a small peak at m/e=100, corresponding to a fragment of $CF_2=CF_2$ present in the mass spectra of the 1,2-substituted hexafluorocyclobutanes which is absent in the 1,3-substituted products. Absolute configurations of the different isomers are not assigned.

This example shows that a compound containing one trifluorovinyl group can be combined with a compound containing two trifluorovinyl groups, the mixture then being heated to cause cyclization of the trifluorovinyl groups to provide a fluid containing perfluorocyclobutane groups. Such fluids are of the type useful as low dielectric hydraulic fluids or lubricants.

Example 16

Preparation of a Fluid Polymer of 1,3-bis(trifluorovinyloxy)benzene (1′, 1″, 2′, 2′,tetrafluorothoxy)-trifluorovinyloxybenzene and 1,3-bis(1′, 1″, 2′, 2′-tetrafluoroethoxy)benzene A mixture (25 ml) consisting of 1,3-bis(trifluorovinyloxy)benzene (as prepared in Example 4) (26 percent), 3-(1′, 1″, 2′, 2′,-tetrafluoroethoxy)trifluorovinyloxybenzene (54 percent), 1,3-bis(1′, 1″, 2′, 2′-tetrafluoroethoxy)benzene (as isolated in Example 4) (15 percent),and tetraglyme (5 percent) is placed in a 100 ml round bottom flask and heated at reflux under nitrogen for 5 hours. The resulting viscous oil is checked by GC and is found to contain unreacted 1,3-bis(1′, 1″, 2′, 2′-tetrafluoroethoxy)benzene and tetraglyme, as well as mixtures of isomers of heavy components. After removal of the light, unreacted components, two fractions are cleanly separated by fractional distillation and each is analyzed by GC/MS.

The first fraction is found to contain primarily 1,2-bis(3′,[1″, 1″, 2″, 2″′-tetrafluoroethoxy]phenoxy) hexafluorocyclobutane as two isomers (cis and trans substituted hexafluorocyclobutane) followed by small amounts (1–2 percent each) of two 1,3-substituted hexafluorocyclobutane products (cis and trans), all having roughly similar mass spectra. The following is the mass spectral data for the first isomer to elute from the chromatography column, and corresponds to one of the 1,2-substituted isomers: m/e: 580 (25.8 percent); 371 (11.3 percent); 321 (12.5 percent); 290 (23.4 percent); 270 (36.4 percent); 243 (69.9 percent); 193 (100.0 percent); 95 (96.4 percent); 92 (55.9 percent); 76 (26.7 percent); 64 (29.9 percent); 51 (21.9 percent).

The second fraction contains 1,3-bis(2′-[3″-{1″′, 1″′, 2″′, 2″′-tetrafluoroethoxy}phenoxy]hexafluorocyclobutyl)phenyl ether, primarily as three isomers of 1,2-substituted hexafluorocyclobutanes with a small amount of four isomers of the product with one 1,2-substituted and one 1,3-substituted hexafluorocyclobutane ring. The seven isomers all give roughly the same peaks in their mass spectra in differing intensities. The following mass spectral data is for the first isomer to elute from the GC column, and corresponds to one of the three main isomers of the product: m/e: 850 (24.7 percent); 540 (24.2 percent); 371 (41.5 percent); 321 (12.9 percent); 301 (16.4 percent); 290 (33.9 percent); 270 (74.4 percent); 243 (63.9 percent); 207 (24.1 percent); 193 (86.7 percent); 173 (14.8 percent); 95 (100.0 percent); 92 (63.2 percent), 76 (71.8 percent)64 (32.6 percent); 51 ( 15.5 percent).

This example shows that a compound containing one trifluorovinyl group may be combined with a compound containing two trifluorovinyl groups in a solvent, the resulting mixture being heated to cause cyclization of the trifluorovinyl groups. Such fluids are of the type useful as low dielectric hydraulic fluids or lubricants.

Example 17

Preparation of 2,5-bis(2-trifluoroethenyloxy)hexane

Sodium hydride (16.5 g, 60 percent dispersion in oil, 0.41 mol) is transferred to an oven dried 2 L 3-necked flask. Dry dimethyl formamide (DMF) (400 mL) is added via syringe and the flask is fitted with a stirrer, thermometer, and septum. The mixture is stirred and cooled in an ice bath as 2,5-hexanediol (17.78 g, 0.15 mol) dissolved in 50 mL of dry DMF is added slowly via syringe. The septum is replaced with a pressure-equalizing addition funnel, and the mixture is allowed to stir overnight. The mixture is cooled to −10 to −15° C. with a dry ice/ethylene glycol bath, and 1,2-dibromotetrafluoroethane (TFDBE) (60 mL, 0.5 mol) is added dropwise to the stirring mixture. The temperature of the reaction is maintained at −10 to −8° C. After one equivalent has been added, foaming is observed, which is allowed to subside before addition of TFDBE is resumed. Some slight foaming is observed for the rest of the reaction. As the reaction approaches completion, large amounts of solid precipitate, which redissolve when the reaction is allowed to warm to 10° C.

The reaction mixture is partitioned between hexane and water. The hexane layer is washed with additional water to remove residual DMF, dried over magnesium sulfate, and concentrated to yield 63.15 g of orange oil. Volatile products are removed by vacuum distillation to yield 36.12 g of colorless oil, which is then chromatographed on alumina with hexane to yield 19.23 g of 2,5-bis(2-bromotetrafluoroethoxy)hexane (26.9 percent yield) and 5.42 g of 2-(2-bromotetrafluoroethoxy)-5-(1,1,2,2-tetrafluoroethoxy)hexane as confirmed by 19 F NMR, 1 H NMR and IR spectra of products. 19 F NMR: (TFA) δ−10.2 (t, J=6 Hz), 8.8 (t, J=6 Hz) HNMR: (TMS)δ1.32 (d, 6H, J=6 Hz), 1.63–1.90 (m, 4H), 4.20–4.78 (m, 2H).

Zinc (1.93 g, 30 mmol) and 2,5-bis(2-bromo-tetrafluoro-ethoxy)hexane (3.45 g, 7.25 mmol) are weighed into a dry 100 mL 3-necked flask. Dry glyme (25 mL) is added via syringe and the resulting mixture is stirred and heated to reflux under nitrogen for 5 hours. The mixture is partitioned between pentane and water. The pentane extracts are dried over magnesium sulfate and concentrated to yield 2.11 g of pale yellow oil. Infrared analysis of this oil indicates the presence of some carbonyl containing impurities. The oil is dissolved in pentane and flushed through a column of neutral alumina to yield, after concentration, 1.33 g (65.8 percent yield) of the desired product. The product is identified by 19 F NMR, 1 H NMR, and IR spectra. 19 F NMR: (TFA) δ46.2 (ddd, J=90 Hz, Jcis=78 Hz, JFH=2 Hz, OCF), 53.8 (d, J=78,=CF cis), 53.9 (d, J=90, =CF trans) HNMR: (TMS) δ1.31 (d, J=6 Hz, 6 H), 1.55–1.90 (m, 4 H), 3.80–4.40 (m, 2 H) IR: $(CM^{-1})$ 1845 $(CF=CF_2)$, 1290 (B,C—O), 1130 (B, C—O).

The material is analyzed by DSC, and exhibits an exotherm of 500 Joules per gram (J/g) at 107° C.

Example 18

Preparation of Methyl 4-(2-bromo-tetrafluoroethhoxy)benzoate, its Conversion to to 4-trifluoroethenyloxybenzoic Acid and the Benzoyl Chloride, and use of the Chloride to Chain Extend Polycarbonate oligomers.

Methyl 4-hydroxybenzoate (304.3 g, 2 mol) is dissolved in 800 mL of methanol and is converted to the potassium salt by the slow addition of potassium hydroxide (132.02 g, 2 mol, 85 percent purity). The resulting mixture is stirred and cooled as necessary to maintain the temperature below 50° C. The solvent is then removed by rotary evaporation and the crystalline salt is dried under vacuum overnight at 140° C.

The dried salt is allowed to cool and transferred to an oven dried 2 L flask under nitrogen. The flask is fitted with a mechanical stirrer, thermometer, heating mantle, condenser and pressure-equalizing addition funnel. Dry dimethylsulfoxide (DMSO) (550 g) is added and the mixture is stirred and warmed to 60° C. as 1,2-dibromotetrafluoroethane (537 g, 2.06 mol) is added slowly. (No appreciable reaction is observed at lower temperatures.) Reaction temperature is o maintained at 65-70° C. for two hours after addition is complete. The mixture is then heated to 90° C. and allowed to cool overnight.

Product is isolated by extracting the mixture with 500 mL of water to remove salts and DMSO. The product separates as an orange oil which is washed with water to remove residual DMSO. (The upper aqueous layer is extracted with methylene chloride, and the methylene chloride solution is evaporated to yield about 40 g of product which is added to the rest of the product prior to the water washes.) The product (623 g) is distilled at 85° C./0.3 mm Hg to yield 561 g of colorless oil, 85 percent yield. The product is identified by 19 F NMR, 1 H NMR, and IR spectra.

To form a salt suitable for formation of the perfluorovinyl ether, another sample of methyl 4-(2-bromotetrafluoroethoxy)benzoate (66.25 g, 0.2 mol) is weighed into a 4-necked 500 mL round-bottomed flask fitted with a condenser, thermometer, mechanical stirrer, and heating mantle. Methanol (300mL) and sodium hydroxide (8.05 g, 0.2 mol) are added to form a mixture which is stirred and heated to reflux for three hours. A sodium carboxylate forms and began to precipitate early in the reaction and is gelled into an almost solid mass after 1.5 hours. The mass is allowed to settle overnight and the solvent is then removed by rotary evaporation.

The sodium carboxylate is dissolved in warm water. A warm solution of zinc acetate (26.35 g, 0.12 mol) in 40 mL of water is added to precipitate the carboxylate as the zinc salt. The salt slurry is then cooled, and the zinc salt is filtered from the solution and dried under vacuum to yield 65.6 g (94 percent yield).

The dried zinc salt is transferred to a dry 4-necked 500 mL round-bottomed flask containing zinc metal (10 mesh, 13.0 g, 0.198 mol). Dry glyme (160 mL) is added by a canula and the flask is fitted with a condenser, mechanical stirrer, and thermometer. The mixture is stirred and heated to reflux under nitrogen overnight. The mixture is acidified by the addition of 18 mL of concentrated HCl, concentrated by rotary evaporation, and then partitioned between methylene chloride and water. The methylene chloride solution of the acid is dried over magnesium sulfate, filtered and concentrated to yield 40.02 g of 4-trifluoroethenyloxybenzoic acid as white crystals (97.6 percent yield, m.p. 139–140° C). The product 4-trifluoroethenyloxybenzoic acid is identified by 19 F NMR, 1 H NMR, and IR spectra.

To form the 4-trifluoroethyloxybenzoyl chloride, 4-trifluoroethenyloxybenzoic acid (79.4 g, 0.36 mol) is transferred to a 1 L round-bottomed flask. Dry methylene chloride (250 mL) is added, and the resulting mixture is stirred under nitrogen as oxalyl chloride (62.5 g, 0.49 mol) is added. The mixture is stirred overnight and then concentrated by rotary evaporation. The brown liquid is distilled at 60–65° C./0.2 mmHg to yield 82.94 g of colorless liquid (97.4 percent yield). The product is identified by 19 F NMR, 1 H NMR, and IR spectra.

To cap an oligomer, a low weight average molecular weight polycarbonate oligomer (2000 MW) terminated with bisphenol A groups (7.5 g, about $7.8 \times 10^{-3}$ mol of phenolic OH) is weighed into a 100 mL flask with the trifluoroethenyloxybenzoyl chloride (1.84 g, $7.8 \times 10^{-3}$ mol). Dichloromethane (30 mL) is added to dissolve the oligomer, and the mixture is stirred as triethylamine (0.81 g, $8 \times 10^{-3}$ mol) is added via syringe. A fine white precipitate forms in the mixture almost immediately. Dichloromethane is added to dissolve the precipitate, forming a dichloromethane solution which is extracted with water to remove triethylamine hydrochloride. The dichloromethane solution is dried over 4A molecular sieves, and concentrated to yield 9.06 g (100 percent yield) of oligomer capped with trifluoroethenyloxy benzoyl groups. Structure is verified by 19 F NMR (trifluorovinyl ether pattern), H-NMR (2 protons of the aromatic benzoate are shifted downfield to 8–8.3 ppm from the aromatic polycarbonate protons), and FT-IR (C=O stretch at 1739 cm$^{-1}$, distinct from the C=O stretch of polycarbonate at 1774 cm$^1$).

A sample of the capped oligomer is heated to 300° C. in a DSC apparatus to effect chain extension. The sample is cooled and reheated to determine the Tg, which is observed at 140.4° C. (representative of high weight average molecular weight polycarbonate). For comparison, a sample of the uncapped oligomer heated to 300° C., cooled, and reheated, exhibits a Tg of only 106.8° C. The increase of 33.6° C. in the Tg is attributed to the production of high weight average molecular weight polycarbonate through the thermal cyclodimerization of the trifluorovinyl ether groups.

Example 19

Reaction of 4,4'-biphenol and trifluorovinyloxybenzoyl Chloride

Dihydroxybiphenyl (0.7888 g, 0.00423 mole) is placed in a dry 250 ml round bottom flask with a magnetic stirring bar. The flask is capped with a rubber septum. Dry methylene chloride (25 ml) and trifluorovinyloxybenzoyl chloride as prepared in Example 18 (2.000 g, 0.00846 mole) are each added to the flask via syringe. The mixture is stirred as triethlyamine (0.86 g, 0.0085 mole) is added dropwise. The mixture is stirred at room temperature for 2 hours, then filtered. A white precipitate is obtained and washed several times with methylene chloride to remove residual triethylamine hydrochloride. A white crystalline product is obtained and has a melting point of 225°–228° C. Qualitative solubility tests indicate that this product is nearly insoluble in methylene chloride, acetone, acetonitrile, hexane, methanol, water and benzene, only slightly soluble in hot tetrahydrofuran, and moderately soluble in carbon tetrachloride.

Infrared analysis (using a potassium bromide KBr pellet) gives the following spectrum (reported in cm-1): 1830, indicative of a trifluorovinyl group; 1723, indicative of a benzoate ester; 1600 and 1495, indicative of aryl carbon-carbon double bond; 1315 and 1267, indicative of carbon-fluorine bonds.

Thermal analysis (DSC) of the monomer indicates a crystalline melt beginning at 223° C., followed immediately by a slight exotherm as the monomer undergoes polymerization. A second scan of the sample shows no thermal activity up to and including 350° C.

The melted monomer exhibits possible liquid crystalline behavior during it's short lived melt phase. As viewed under a cross-polarized light microscope, the melted monomer phase (at 230° C.) exhibits birefringence suggestive of liquid crystalline behavior, followed by rapid polymerization to a crystalline solid. This solid does not melt, but undergoes discoloration and apparent decomposition when heated in air at temperatures above 400° C.

Example 20

Preparation of Polyesters from 1,2-bis(4-chloroformylphenoxy)hexafluorocyclobutane by Solution Polymerization Methyl p-hydroxybenzoate is converted to its potassium salt by reaction with a stoichiometric amount of potassium hydroxide in methanol. The salt is isolated by evaporation and dried under vacuum. The dried salt is slurried in an equal weight of dry dimethyl sulfoxide. The mixture is stirred and heated to about 50° C. and a slight excess of 1,2-dibromotetrafluoroethane is added slowly. The reaction temperature is maintained at 60-70° C. An efficient condenser is necessary to condense the dibromotetrafluoroethane. After addition is complete, the mixture is warmed for an additional hour, cooled and poured into an equal volume of water. The product (methyl 4-(2-bromotetrafluoroethoxy)benzoate) separates as a brown oil which is distilled under vacuum (85-90° C., 0.3 torr) to yield a colorless oil (85-95 percent yield).

The bromotetrafluoroethylether is dehalogenated by combining it with a stoichiometric amount of granular zinc in glyme and refluxing overnight. After removal of the glyme by evaporation, the product, methyl 4-trifluoroethenyloxybenzoate, is distilled under vacuum (85-90° C./8-10 mmHg, 85-100 percent yield).

The methyl 4-trifluoroethenyloxybenzoate is cyclodimerized by heating at 195° C. for several hours. The dimerized product is isolated by distillation (135-150° C./0.025 mmHg, 97 percent yield, with the remainder being unreacted vinyl compound). The overall yield from methyl p-hydroxybenzoate is 80 percent.

The dimer is saponified to the diacid with 2.1 molar equivalents of sodium hydroxide in methanol. Upon acidification with concentrated hydrochloric acid the diacid precipitates and is filtered from the liquid as an insoluble white powder with a melting point above 300° C. Yields are quantitative. The diacid is converted to the diacid chloride by slurrying it in approximately a 6 molar equivalent of thionyl chloride and warming the mixture to 50-75° C. The product diacid chloride is soluble in dichloromethane and is purified by dissolving the crude reaction product in dichloromethane and filtering the diacid chloride solution from unreacted diacid (which is insoluble). The product is identified by 19 FNMR, HNMR and infrared (IR) spectra. IR 1790, 1755 cm$^{-1}$ (C=O) no CO$_2$H absorption.

Bisphenol AP (1,1-bis(4-hydroxyphenyl)-1-phenyl ethane) (6.14 g, 21.1 mmol) is transferred to a dried resin kettle (a reaction vessel with a large top that clamps onto the vessel) along with 50 mL of dry dichloromethane. The mixture is stirred under nitrogen as triethylamine (5.9 mL, 42.2 mmol) is added via syringe. The solution is stirred and cooled in a water bath as a solution of 1,2-bis(4-chloroformylphenoxy)- hexafluorocyclobutane (10.0 g, 21.1 mmole)in dichloromethane (50 mL) is added via syringe. The mixture is allowed to stir overnight under nitrogen to form a polymer in solution.

The polymer is then capped by adding 0.25 mL of 4-trifluoroethenyloxybenzoyl chloride (as prepared in Example 18) to the solution with stirring. The solution is diluted with 200 mL of dichloromethane and washed with water to remove triethylamine hydrochloride until a sample of the water washes added to a 5 percent silver nitrate solution produces no silver chloride precipitate. The polymer solution is then poured into a glass dish, and the dichloromethane is allowed to evaporate overnight, leaving a clear, tough film, which is dried under vacuum at 140° C. and is weighed. (Yield=14.58 g, 99.9 percent).

Example 21

Preparation of Polyesters from 1,2-bis(4-chloroformylphenoxy)hexafluorocyclobutane by Emulsion Polymerization Bisphenol AP (10.51 g, 36 mmol) is transferred to a blender container along with water (200 mL), 50 percent aqueous sodium hydroxide (6.6 g, 82 mmol) and benzyltrimethylammonium chloride (2 g, 6.5 mmol, 60 percent aqueous solution). Agitation is supplied by a blender plugged into and having its speed controlled by a Variac. The mixture is agitated at 25-30 percent power until the bisphenol AP dissolves.

1,2-bis(4-chloroformylphenoxy)hexafluorocyclobutane (prepared as in Example 20) (17.12 g, 36 mmol), is dissolved in 70 mL of dichloromethane to form a diacid chloride solution and is chilled in an ice bath. Dichloromethane (25 mL) is added to the blender, which is agitated at 30 percent power for 2 minutes, at which time the chilled diacid chloride solution is added to the blender over a period of 20 seconds to form an admixture. The container in which the diacid chloride mixture is chilled is rinsed with 30 mL of dichloromethane, which is added to the admixture. The admixture is agitated at 40 percent power for 12 minutes; then 1.2 mL of benzoyl chloride is added. The admixture is agitated for an additional 2 minutes. Then agitation is stopped and layers are allowed to separate. An aqueous layer is decanted, and a lower, dichloromethane layer, is agitated with 200 mL portions of deionized water until a sample of the water tests negatively for chloride ion.

Addition of an equal volume is isopropyl alcohol to the volume of dichloromethane layer precipitates a polymer from the dichloromethane solution as a thick, viscous mass. The polymer is allowed to dry, then redissolved in dichloromethane to form a clear solution and poured into a glass dish. Evaporation of the dichloromethane overnight yields a tough clear film which is dried under vacuum at 140° C. Weight of recovered polymer is 24.56 g, 98 percent yield.

Examples 22–28

Polyesters Prepared using 1,2-bis(4-chloroformylphenoxy)hexafluorocyclobutane The process of Example 20 for the solution preparations and the process of Example 21 for the emulsion preparations are repeated using the following bisphenols with the results indicated in the following table, which includes polymers of Examples 20 and 21 for comparison:

| Ex. No. | Bis-phenol** | Yield (percent) | Tg (°C.) | weight average | polymerization method | dielectric constant/ dissipation factors at 1 KHz |
|---|---|---|---|---|---|---|
| 22 | Bisphenol A | 100 | 137 | 47000 | solution | 2.93/ 0.0031 |
| 20 | Bisphenol AP | 99.9 | 178 | 60000 | solution | 3.05/ 0.0042 |
| 23 | Bisphenol AF | 97 | 160 | 66000 | solution | 2.94/ 0.0036 |
| 24 | 4,4'-Biphenol | 98 | >400 | * | solution | — |
| 25 | Hydroquinone | 99 | >400 | * | solution | — |
| 26 | Bisphenol A | 100 | — | 64000 | emulsion | — |
| 21 | Bisphenol AP | 98 | 185 | 104000 | emulsion | — |
| 27 | Bisphenol AF | 100 | — | 79000 | emulsion | — |

*These materials are highly crystalline and precipitate from the reaction mixture. Molecular weights can not be determined by GPC due to insolubility.
**Bisphenol AF is 2,2-bis(4-hydroxyphenyl)-hexafluoropropane; bisphenol A is 2,2-bis(4-hydroxyphenyl)propane Tensile and flexural strength are determined for a sample of the bisphenol A polymer prepared by solution polymerization (Example 22).

Tensile strength is 6460 pounds/square inch.
Flexural strength is 3060 pounds/square inch.
Flexural Modulus is 330,000 pounds/square inch.

Example 28

Polymerization of 1,2-bis(4-ethynylphenoxy)hexafluorocyclobutane p-Ethylphenol is dissolved in methanol to form an admixture. A methanolic solution of one equivalent of potassium hydroxide is added to the stirring admixture. The admixture is cooled to maintain a temperature below 40° C. Stirring and cooling is maintained for about 15 minutes after addition is complete.

The methanol is then removed by rotary evaporation and a resulting wet salt is transferred to a suitable container and dried under vacuum at 100–140° C. to produce a dry salt. The dry salt is transferred to a dry flask and an equal volume of dry DMSO is added to form a slurry. The flask is fitted with a mechanical stirrer, thermometer, efficient condenser, and pressure-equalizing addition funnel.

The salt slurry is stirred and cooled to <20° C. as a slight excess (1.1 equivalents) of 1,2-dibromotetrafluoroethane is added slowly. The reaction is heated to 60° C. for about 2 hours after addition is complete.

The 2-bromotetrafluoroethyl ether is isolated by pouring into an equal volume of water. The ether separates as a lower layer of oil and is purified by vacuum distillation.

4-Trifluorovinyloxy-1-ethylbenzene is synthesized by combining the 2-bromotetrafluoroethyl ether with granular zinc in dry glyme and refluxing at 85–90° C. with stirring overnight.

After completion of the reaction, the precipitated zinc salts are removed by centrifugation. The glyme is removed by rotary evaporation and the product, 4-trifluorovinyloxy-1-ethylbenzene, is purified by vacuum distillation.

4-Trifluorovinyl-1-ethylbenzene is cyclodimerized by heating to 180–195° C. for 8 hours. Low boiling impurities and unreacted perfluorovinyl compound are removed by vacuum distillation. The product 1,2-bis(4-ethylphenoxy)hexafluorocyclobutane is distilled under vacuum (110° C./0.05 torr) 40 percent yield from 4-ethylphenol and have the characteristics reported in Table 3.

A 5 g sample of 1,2-bis(4-ethynylphenoxy)hexafluorocyclobutane (as prepared in Example 20) is thermally cured at 180° C. for 3 hour followed by a postcure at 250° C. for 30 minutes. The density of the polymer is 1.34 g/cc. Dielectric constant is 2.6 at 1 KHz.

DSC analysis of 1,2-bis(4-ethynylphenoxy) hexafluorocyclobutane indicates a broad exotherm starting at 160° C and ending at 280° C. with delta H=632 Joules/g. The initially colorless oil turns into a clear, dark red solid which is analyzed by DSC, TMA, and TGA (Thermogravimetric analysis). TGA (20° C./min., nitrogen sweep) of the cured sample shows: 2 percent loss at 400° C., 5 percent loss at 470° C., 35 percent loss at 580° C, and 80 percent loss at 900° C. No Tg is observed up to 350° C. by DSC or TMA.

Example 29

Synthesis of 3-(2Bromotetrafluoroethoxy)aniline

Dimethylsolfoxide (1.0 liter) (DMSO) and m-xylene (250 ml) are combined in a 2.0 liter round bottomed flask fitted with a Dean-Stark trap topped with a reflux condenser, and the solution is purged with nitrogen for 10 minutes. 3-Aminophenol (100.0 g, 0.917 mole) is added and stirred to dissolution with continued nitrogen purge. An aqueous solution of KOH (45 percent by weight, 114.3 g, 0.917 mole) is added all at once, and a nitrogen purge is continued for 5 minutes. The system is evacuated to a pressure of 100 mm Hg (13.32 kPa) absolute pressure, and heating is begun in order to remove water azeotropically. The temperature of the refluxing solution is initially 81° C., rising to as high as 96° C. as water is removed. Water removal is carried out for 24 hours. The resulting phenoxide salt solution tests at 240 ppm water by Karl-Fisher titration. A portion of the m-xylene (200 ml) is removed by distillation under vacuum. The reaction mixture is cooled to 25° C., and 1,2-dibromotetrafluoroethane is added slowly over 30 minutes, and a slow exotherm follows. Temperature is controlled to 30° C.±2° C. The resulting mixture is heated to 45° C. overnight. The resulting product mixture contains approximately 40 percent by weight of the desired product 3-(2-bromotetrafluoroethoxy)aniline, with the remainder being the by-product 3-(1,1,2,2,-tetrafluoroethoxy)aniline. These two components are separated by fractional distillation using a 10 inch (0.64 m) long, 24/40 standard taper jointed reflux condenser packed with distillation packing commercially available from Ace Glass Co. under the trade designation Pro-Pak TM as a distillation column. The by-product boils at 46°–48° C. and 0.25 mm Hg (33.3 Pa) absolute pressure, and the desired product 3-(2-bromotetrafluoroethoxy)aniline boils at 52°–54° C. and 0.25 mm Hg (33.3 Pa) absolute pressure. A total of 47.2 g (0.164 mole, 16.8 percent yield) is isolated by this method.

GC/MS analysis, m/e (percent): 63 (76.4), 64 (28.2), 92 (35.0), 286 (10.9), 287 (68.5), 288 (22.6), 289 (62.0), 290 (14.0), 301 (87.1), 302 (21.6), 303 (100), 317 (78.4), 318 (21.1), 319 (69.8), 320 (10.6).

Example 30

Synthesis of 4-(2-bromotetrafluoroethoxy)nitrobenzen and the Corresponding Aniline A solution of DMSO (250 ml) and m-xylene (50 ml) is added to a 1 liter 5-necked round-bottomed flask and purged thoroughly with nitrogen. Powdered 4-nitrophenol (50.0 g, 0.35 mole) is added to the stirring solution, followed by KOH pellets (87.4 weight percent (remainder water) pellets, 23.1 g, 0.36 mole). The mixture is heated to 100° C. to dissolve the KOH, and then cooled to 82° C. The system is then evacuated to 100 mm Hg (13.32 kPa) absolute pressure and water is removed by azeotropic distillation into a Dean-Stark trap. After water removal is continued overnight a portion of the xylene (40 ml) is removed by vacuum distillation through the Dean-Stark trap and the remaining solution is measured at 105 ppm water by Karl-Fisher titration. The fluorocarbon 1,2-dibromotetrafluoroethane (100.0 g, 0.385 mole) is added at a temperature of 35° C. The reaction mixture is then heated to 74° C. for 48 hours, with a chilled reflux condenser ($-5°$ C.) providing reflux of the fluorocarbon. The DMSO and xylene are removed by evaporation the remaining brown liquid is filtered to remove salts. The flitrate is distilled on a rotary evaporator at 2 mm Hg absolute pressure and 120° C. The resulting product, 4-(2-bromotetrafluoroethoxy)nitrobenzene (53.6 g, 46.8 percent yield) is greater than 99.5 percent pure as by GC/MS analyzed by analysis.

GC/MS, m/e (percent): 58 (12.0), 63 (76.5), 64 (28.2), 92 (35.0), 286 (10.9), 287 (68.5), 288 (22.6), 289 (62.0), 290 (13.9), 301 (87.1)302 (211.6), 303, (100), 317 (78.4), 21.1), 319 (69.0), 320 (10.6).

4-(2-Bromotetrafluoroethoxy)aniline

The product of the previous reaction, 4-(2bromotetrafluoroethoxy)nitrobenzene (20.0 g, 0.069 mole), is added to a 50 percent by volume solution of ethyl alcohol in water (30.0 g) and powdered iron filings (11.0 g, 0.20 mole) in a 250 ml 3-necked round bottomed flask fitted with a nitrogen padded reflux condenser and a dropping addition funnel. The mixture is purged thoroughly with nitrogen, and brought to reflux. A solution of concentrated HCl (1.3 ml, 0.0156 mole) in 8 ml ethanol/water (1:1 by volume) is added slowly drop wise over 30 minutes. The resulting reaction mixture is refluxed for 3 hours, then cooled to room temperature. The mixture is filtered and the solids are washed twice with dilute KOH (10 ml each, 0.01M), just enough to make the flitrate up to pH 7. The solids are then washed with acetone (25 ml) and the acetone wash is added to the flitrate. The flitrate phase-separates, and the lower phase is removed and distilled on a rotary evaporator (2.0 mm Hg (2.66 kPa), 100° C.) to recover the pure product (7.47 g, 0.026 mole, 37 percent yield) as a water white oil in greater than 99 percent purity.

GC/MS, m/e (percent): 53 (11), 80 (42.4), 108 (100), 287 (53.1), 288 (17.0), 289 (51.0), 290 (11.3).

Example 31

Synthesis of Trifluorovinyloxyanilines

Freshly activated zinc metal (2.0 g, 0.0306 mole) and dry acetonitrile (25 ml, less than 200 ppm $H_2O$) are placed in a 250 ml round bottomed flask fitted with a mechanical stirrer and a nitrogen padded reflux condenser. The stirred mixture is heated to reflux and the product of the above reaction, 4-(2-bromotetrafluoroethoxy)aniline (7.47 g, 0.026) in 5 ml dry acetonitrile is added over 15 minutes. The resulting mixture is refluxed for 3 hours, then decanted away from unreacted zinc metal, evaporated to dryness, washed with 3M HCl solution (100 ml) to removed zinc salts, water (50 ml), 15 percent by weight KOH solution to neutralize the residual acid, and then evaporated. The residue is distilled on a rotary evaporator under high vacuum (2 mm Hg absolute) (0.267 kPa) at 100° C. This distillate, containing both the desired product 3-trifluorovinyloxyaniline and the by-product 3-(1,1,2,2,-tetrafluoroethoxy)aniline, is purified by column chromatography on neutral alumina using 15 percent dichloromethane in hexane as an eluent. A total of 2.0 g (0.0105 mole, 40.7 percent yield) is isolated by this method in >95 percent purity.

GC/MS analysis, m/e ( percent): 142 (18.6 percent), 188 (12.2 percent), 189 (100 percent), 190 (38.2 percent).

Example 32

Synthesis of N,N-Bis(4-trifluorovinyloxy)-3,3',4,4'-benzophenonetetracarboxylic Diimide The product of Example 31, 4-trifluorovinyloxyaniline (1.5 g, 0.00793 mole) and N-methylpyrrolidinone (12.0 ml) are placed in a 100 ml, 3-necked round bottomed flask equipped with a mechanical stirrer and purged thoroughly with nitrogen. A sample of 3,3',4,4',-benzophenonetetracarboxylic dianhydride (1.02 g, 0.00317 mole) is added to the stirred solution all at once, and the mixture is stirred for 2.5 hours to form the amic acid intermediate. Dry sodium acetate (0.90 g) is added to the reaction mixture, followed by acetic anhydride (1.30 g). The reaction mixture immediately turns cloudy, and within minutes is a solid slurry. This slurry is heated to 90° C. for 20 minutes, then allowed to cool. After stirring overnight the mixture is filtered on a coarse grained fritted glass filter and the collected solids are washed with hexane (25 ml). The solid crystals are air dried for 30 minutes, followed by drying in a vacuum drying oven at 100° C. A total of 2.01 g of material is collected (95.5 percent yield). The final product has a melting point of 223°–225° C., at which point the material fuses into a solid mass, indicative of polymerization of the product immediately upon heating at these temperatures.

FTIR analysis indicates the presence of imide bonds in the product. IR ($cm^{-1}$): 1722, 1656, 1398, 1123 (imide); 1220, 1196, 1165, 1137, 1103 (C-O, C-F); 1514 (aromatic).

Example 33

Synthesis of 3-(2-bromotetrafluoroethoxy)phthalig Anhtdride

Preparation of 4-(2-Bromotetrafluoroethoxy)-1,2-dimethylbenzene, Reaction of 3,4-Xylenol with Dibromotetrafluoroethane Xylenol (150.0 g, 1.2278 mol) is weighed into a 1 L rotovap flask and dissolved in 500 mL of methanol. The solution is sparged with nitrogen for 5 minutes and then potassium hydroxide (81.05 g, 1.2278 mol) is added in portions to the solution with stirring. After all the KOH has dissolved, the solution is concentrated to a thick syrup by rotary evaporation and then transferred into a Pyrex TM baking dish and dried under vacuum overnight at 130–150° C. The dried salt is broken up and transferred along with 784 g of dry DMSO (500 ppm water) to a 2 L five-necked round-bottomed flask which is then equipped with a stirrer, ice bath, nitrogen inlet, addition funnel, and thermometer. Dibromotetrafluoroethane (162 mL) is added slowly to the stirred, ice-cooled reaction at such a rate sufficient to maintain the temperature between 15 and 25° C. After addition is complete, the reaction is allowed to stir overnight at room temperature and then warmed to 50° C. for 30 minutes. The mixture is then allowed to settle, and the DMSO solution is decanted from the precipitated salts.

GC analysis indicates a good yield of bromotetrafluoroethyl ether with only a small amount of hydrogen ether. The DMSO solution is extracted with hexane (addition of a small amount of 1M aqueous HCl facilitates the separation of the layers). The hexane solution is back-extracted with water and base and concentrated by rotary evaporation. The resulting brown oil (348.10 g, 94 percent pure, 94.5 percent crude yield) is fractionally distilled under vacuum(65–70° C., 2.75 mm Hg 0.367 kPa) to remove the hydrogen ether by-product. The product, 4-(2-bromotetrafluoroethoxy)- 1,2-dimethylbenzene, is then distilled at 70–85° C. (1 mm Hg 0.133 kPa) to give 318.75 g of colorless oil. F-19 NMR: (relative to trifluoroacetic acid as 0 ppm) -8.12 (triplet, $CF_2Br$, J=4 Hz), 9.77 (triplet, $OCF_2$, J=4 Hz); H-1 NMR (CDCl$_3$): delta 2.22 (singlet, $CH_3$), 2.24 (singlet, $CH_3$), 6.92–7.11 (multiplet, 3 H); C-13 NMR (CDCl$_3$): (ppm) 19.2 ($CH_3$), 19.8 ($CH_3$), 113.9 ($CF_2$, triplet of triplets, $J_{geminal}$=313 Hz, $J_{vicinal}$=45 Hz), 115.9 ($CF_2$, triplet of triplets, $J_{geminal}$=313 Hz, $J_{vicinal}$=45 Hz), 118.8, 122.7, 130.6, 135.4, 138.4, 146.8.

Oxidation of 4-(2-Bromotetrafluoroethoxy)-1,2-dimethylbenzene to 4-(2-Bromotetrafluoroethoxy)phthalic Anhydride Xylenol bromotetrafluoroethyl ether (20.0 g, 0.0664 mol) is weighed into a 500 mL three-necked flask along with cobalt acetate hydrate (0.85 g, 0.0034 mol), sodium bromide (0.35 g, 0.00332 mol) and methyl ethyl ketone (0.82 g, 0.0113 mol). Propionic acid (250 mL) is added and the flask is equipped with a condenser, gas sparge tube, magnetic stirbar, thermometer, and air outlet. The flask is lowered into a hot oil bath maintained at a temperature of 145° C. and the mixture is heated and stirred as air is introduced under the surface of the solution at a rate of 1 cubic foot per hour (28.3 L/h or 472 mL/min). The reaction is followed by sampling at intervals and analyzing by LC (liquid chromatography.) After 4 h at 135° C. (internal temperature) almost all of the starting material disappears and one peak is seen at 15.78 minutes (this is probably the monoacid).

Heating is continued overnight. LC analysis of the reaction after a total of 20 hours shows a complex series of peaks. Propionic anhydride is added (5 mL) and heating is continued. After 48+22 additional hours of heating at 135–140° C. the desired product is seen in the LC at about 14 minutes (35 percent by LC). There is some white precipitate visible on the walls of the flask; an additional 5 mL of propionic anhydride is added and heating is continued for 1 hour. LC analysis after this treatment shows the anhydride peak to be 44 percent of the mixture. Heating is continued, and after 6 hours the anhydride peak is 54 percent (by LC) of the mixture. The mixture is allowed to cool and then concentrated by rotary evaporation. The residue, a dark blue oil is distilled under vacuum. A clear liquid is distilled from the mixture at 120–125° C. (0.7–1 mm Hg (0.093–0.133 kPa)), which develops a greenish cast upon standing. The yield of liquid is 19.57 g (85.9 percent yield).

NMR analysis indicates that this product is mainly the anhydride. F-19 NMR: (relative to trifluoroacetic acid as 0 ppm) −7.38 (triplet, $CF_2Br$, J=4.5 Hz), 10.34 (triplet, $OCF_2$, J=4.5 Hz); H-1 NMR (CDCl3): delta 7.0–8.11 (multiplet); C-13 NMR (CDCl3): 117.8, 127.7, 128.8, 133.4, 154.5, 161.2, 169.7 (C=O), 176.1 (C=O), (signals from the $CF_2$ are too small to assign shifts).

4-(Trifluorovinyloxy)- 1,2-dimethylbenzene

Acetonitrile (200 mL) and zinc (50 g, 0.765 mol) are transferred to an oven-dried two liter three-necked Morton flask fitted with a mechanical stirrer, reflux condenser, and thermocouple. The mixture is stirred and heated to 50° C. by means of a heating mantle and temperature controller. The mixture is assayed for water (700 ppm) and the temperature is increased to 65° C. The bromofluoroethyl ether, 3,4-dimethyl-l-(2-bromotetrafluoroethoxy)benzene (187.04 g, 0.621 mole) is added over a period of thirty minutes to the stirring mixture. The temperature of the mixture is then increased to 77° C. and the mixture is stirred overnight. Gas chromatographic analysis of the mixture shows no remaining starting material. The mixture is transferred to a 2 L round-bottomed flask using hexane and water to rinse out the reaction vessel. The solvents (water, hexane and acetonitrile) are then removed by rotary evaporation at 65° C. and 100 mm Hg (13.33 kPa). Under these conditions a small amount of the product is carried over with the solvent. The pressure is then reduced to about 2 mm Hg (0.26 kPa) which causes the product, monomer, 3,4-dimethylphenyl perfluorovinyl ether, to distill over as a clear liquid. Yield 108 g (87 percent yield, purity 94 percent).

1,2-Bis(3,4-dimethylphenoxy)hexafluorocyclobutane- Dimerization of 4-(Trifluorovinyloxy)-1,2-dimethylbenzene The perflurovinyl ether (77.11 g) is dimerized by heating at 180–195° C. for 6 hours and then distilled under vacuum to yield the 1,2-bis(3,4-dimethylphenoxy)perfluorocyclobutane as a light yellow oil (180° C., 0.7 mm Hg), (70.4 g, 91.3 percent yield). An additional 5 g of product is collected which contains about 2 percent perfluorovinyl ether along with the dimers, cis and trans 1,2-bis(3,4-dimethylphenoxy)hexafluorocyclobutane. H-1 NMR (CDCl3): δ[2.08 (s, $CH_3$), 2.10 (s,$CH_3$), 2.11 (s, $CH_3$), 12 H], 6.89–6.96 (m,6 H). C-13 NMR (CDCl3): (ppm) 18.9 ($CH_3$) and 19.8 ($CH_3$), 105–107

(small complex multiplet CF$_2$), 108.5–110.8 (small complex multiplet, CF$_2$), 113.1–113.9 (small complex multiplet, CF$_2$), 115.2–115.8 (small complex multiplet, CF$_2$), 117.9–119.8 (small complex multiplet, CF$_2$), 115.3 and 115.8, 119.8 and 120.0, 130.7 and 130.8, 133.71 and 134.0, 138.5 and 138.6, 151.0 and 151.1. F-19 NMR (CDCl3): (ppm) 50.62–50.64 (m), 51.91–52.08 (m), 52.84–53.06 (m), 53.52–53.56 (m), 54.11–54.23 (m), 54.26–54.29 (m), 54.47–54.51 (m), 54.56–54.71 (m)55.23 (bs), 55.67–55.69 (m), 56.37–56.39 (m).

1,2-Bis(3,4-dicarboxyphenoxy)hexafluorocyclobutane - Oxidation of 1,2-Bis(3,4dimethylphenoxy)hexafluorocyclobutane The dimer (40.44 g, 86.6 mmol) is weighed into a 500 mL three-necked flask along with cobalt acetate dihydrate (2.49 g, 8.6 mmol), sodium bromide (1.03 g, 8.6 mmol) and methyl ethyl ketone (3 mL, 34 mmol). Propionic acid (350 mL) is added and the mixture is stirred and heated in an oil bath (150° C.) to an internal temperature of 125–135° C. as air is bubbled into the mixture at the rate of 28.3 liters per hour. The reaction is continued for 24 hours then checked by LC analysis. The products appear to consist of mixed acids and anhydrides, so propionic anhydride (5 mL) is added and the reaction is continued. After a total time of 40 hours of heating, a large amount of precipitate is observed on the sides of the flask. Propionic acid (50 mL) is added and the reaction is continued for 4 hours (precipitate dissolved) and then allowed to cool. The mixture is concentrated by rotary evaporation and the residue is dissolved in dichloromethane and washed with cold water. The solution is dried over magnesium sulfate and concentrated by rotary evaporation to give the bisanhydride product as an off-white solid.

Example 34

Synthesis of 3-trifluorovinyloxy-N-(4-trifluorovinyloxyphenyl)phthalimide 3-(2-Bromotetrafluoroethoxy)-N-(4-(2-bromotetrafluoroethoxy)phenyl)phthalimide Into a 250 ml round bottomed flask fitted with a mechanical stirrer and a Dean-Stark trap is placed 4-(2-bromotetrafluoroethoxy)aniline (3.4 g, 0.0118 mole) in 40 ml of N-methylpyrrolidinone (NMP). In a separate flask, 3-(2-bromotetrafluoroethoxy)phthalic anhydride (3.0 g, 0.00874 mole) is dissolved in 20 ml of NMP and is added slowly drop wise over 15 minutes to the stirring solution of 4-(2-bromotetrafluoroethoxy)aniline in NMP. The mixture is stirred for 30 minutes at room temperature, after which m-xylene (6 ml) is added and the suspension is heated to 40° C. After heating at 40° C. for 1 hour the is heated to reflux (181° C.) and is refluxed for 6.5 hours to remove water azeotropically. Upon cooling the solvent is removed by evaporation under vacuum and the solid precipitate is recrystallized from dichloromethane/hexane solution (2:1) to provide the product as a light yellow crystalline solid (4.37 g, 81.5 percent yield) with a melting point of 172°–172.5° C.

Mass spectrum, m/e (percent): 100 (5.2), 431 (6.1), 432 (6.47), 433 (7.97), 611 (7.5), 613 (100), 615 (9.5).

3-Trifluorovinyloxy-N-(4-trifluorovinyloxyphenyl)phthalimide

The product of the previous preparation, 3-(2-Bromotetrafluoroethoxy)-N-(4-(2-bromotetrafluoroethoxy)phenyl) phthalimide, (2.73 g, 0.00445 mole) is dissolved in 20 ml of warm acetonitrile (approximately 50° C.) and added to zinc metal (0.61 g, 0.0093 mole) in 5 ml of acetonitrile stirring at reflux. The reaction mixture is stirred at reflux for 12 hours, then filtered on a fine-pored fritted glass funnel to remove unreacted zinc and zinc halide salts. The precipitate is washed twice with 25 ml of dichloromethane, and the filtrates are combined with the acetonitrile flitrate and evaporated to dryness. The dry residue is dissolved in 15 ml of dichloromethane/hexane (1:1, v/v (volume/volume)) and subjected to column chromatography on neutral alumina using dichloromethane/hexane (1:4, v/v) to provide the product (1.54 g, 83.4 percent yield) as a light yellow solid with a melting point of 160°–160.5° C. IR (cm$^{-1}$): 1721, 1708, 1322, 1121 (imide), 1289, 1282, 1273, 1213, 1191, 1166, 1146, 1110, 1096 (C-O, C-F), 1514, 808, 801,743 (aromatic).

Mass Spectrum, m/e (percent): 103 (10.1), 221 (9.0), 318 (3.5), 414 (5.0), 415 (100), 416 (21.6).

Example 35

Example of Melting Point Depression of Imide Monomers by Combining with other Monomers A sample of the monomer 3-trifluorovinyloxy-N-(4-trifluorovinyloxyphenyl)phthalimide (0.001 g)is packed into a melting point capillary tube (hereinafter tube #1) and placed in a melting point determination apparatus commercially available from Laboratory Devices, Cambridge, Mass. under the trade designation Meltemp. A second tube (hereinafter tube #2) is packed with the monomer 4,4'-bis(trifluorovinyloxy)biphenyl (0.001 g), prepared in Example 1. A third capillary tube (hereinafter tube #3) is packed first with the imide monomer 3-trifluorovinyloxy-N-(4-trifluorovinyloxyphenyl)phthalimide (0.001 g) and then the monomer 4,4'-bis(trifluorovinyloxy)biphenyl (0.001 g). The melting point apparatus is turned on and the melting points of the contents of the three capillary tubes is monitored. The sample of pure monomer 4,4'-bis(trifluorovinyloxy)biphenyl (0.001 g) in tube #2 melts at 44.0°–445.° C. Likewise the monomer 4,4'-bis(trifluorovinyloxy)biphenyl in tube #3 also melts at 44.0°–44.5° C., and flows down into the monomer 3-trifluorovinyloxyoN-(4-trifluorovinyloxyphenyl)phthalimide, which then dissolves in the melted monomer to provide a water white liquid mixture of monomers at 60° C. The pure sample of the monomer 3-trifluorovinyloxy-N-(4-trifluorovinyloxyphenyl)phthalimide in tube #1 melts at 160.0°–160.5° C.

This example demonstrates that imide-containing monomers may be melted at temperatures that are significantly lower than their natural pure melting points by blending with other trifluorovinyl ether monomers. These mixtures provide polyimide-containing polymers which may be processed from the melted monomer stage with a greatly expanded processing window (liquid state with a large difference between melting point and cure temperature) as compared to the pure imide monomers, which tend to melt at high temperatures and provide a shorter processing time between melting and curing processes.

What is claimed is:

1. A process of preparing a polymer having perfluorocyclobutane rings comprising the steps of:
    (a) contacting oligomers having at least two dimerizable perfluorovinyl end groups, and (b) exposing the monomers to a temperature of at least about 50° C. for a sufficient time that a resulting polymer containing perfluorocyclobutane rings is formed wherein the oligomer is an aromatic polyester, aromatic polyamide or polyimide or mixture thereof.

2. The process of claim 1 wherein the perfluorovinyl group is a perfluorovinyl aromatic ether.

3. The process of claim 2 wherein the monomer has a structure represented by:

wherein Ar is an aromatic group.

4. The process of claim 1 wherein the polymer is formed in a shaping apparatus.

5. The process of claim 4 wherein the shaping apparatus comprises an extruder, a compression mold or an injection mold.

6. The process of claim 5 wherein the oligomers have a viscosity suitable for introducing into the shaping apparatus.

7. The process of claim 1 wherein the resulting polymer is solid.

8. The process of claim 1 wherein the oligomer comprises a liquid crystal polymer.

9. The process of claim 1 wherein the oligomer comprises an aromatic polyester.

10. The process of claim 1 wherein the oligomer comprises an aromatic polyamide.

11. The process of claim 1 wherein the oligomer comprises a polyimide.

12. The process of claim 11 wherein polyimide is an aromatic polyimide.

13. The process of claim 1 wherein the resulting polymer is comprises oligomer fragments (repeating units) linked by perfluorocyclobutane rings.

14. The process of claim 13 wherein the oligomer comprises a polyimide.

15. The process of claim 14 wherein polyimide is an aromatic polyimide.

16. The process of claim 1 wherein the oligomer comprises repeating units derived from at least one of Formula IV, V, XIXa, XIXb, or XIXc:

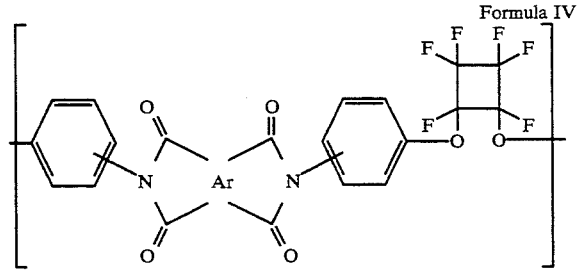
Formula IV with ortho or meta substituted aniline ether rings

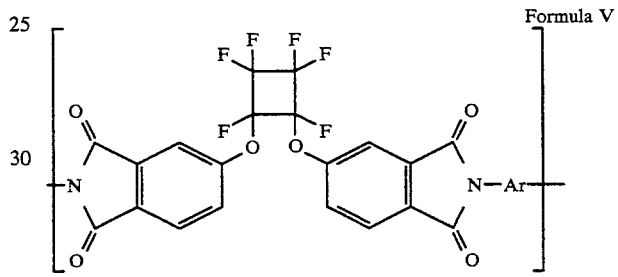
Formula V wherein Ar is an aromatic group

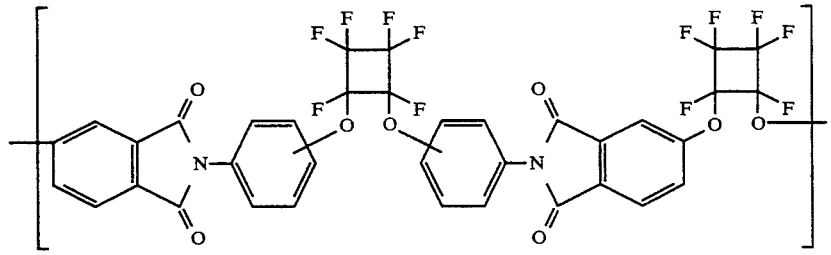
XIXa

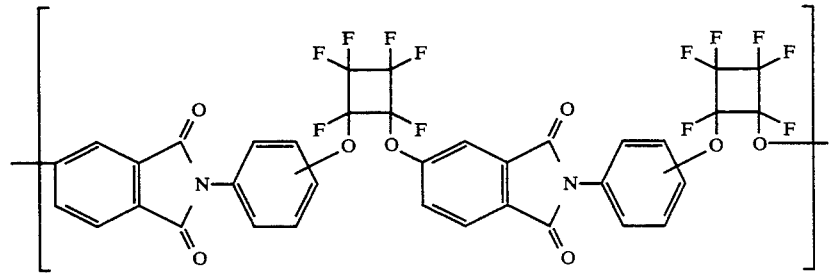
XIXb

OR

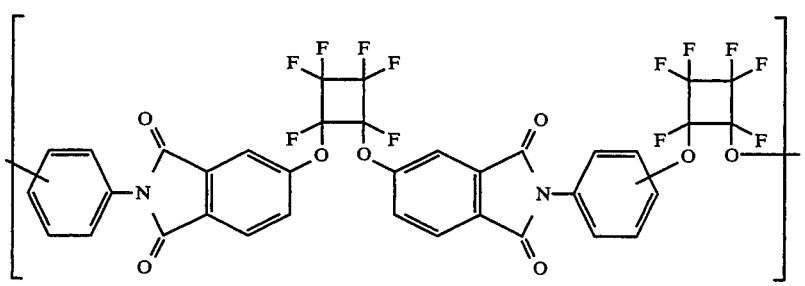

XIXc

XIX a,b, and c all with meta or para substituted aniline-ether aromatic rings.

17. The process of claim 16 wherein the aromatic group is unsubstituted or inertly substituted and has from 1 to about 10 aromatic rings.

18. The process of claim 17 wherein there are from 1 to 5 aromatic rings which are carbocyclic.

19. The process of claim 16 wherein Ar is selected from unsubstituted or inertly substituted phenylene; biphenylene; oxydiphenylene; 9,9-bis(phenyl)fluorene; naphthalene; 2,2-bis(phenyl)hexafluoropropane; 1,1,1-tris(phenyl)trifluoroethane); spiro[fluorene-9,9'-xanthene]or benzophenone.

20. The process of claim 16 wherein the oligomer has repeating units of a structure represented by at least one of the following formulas:

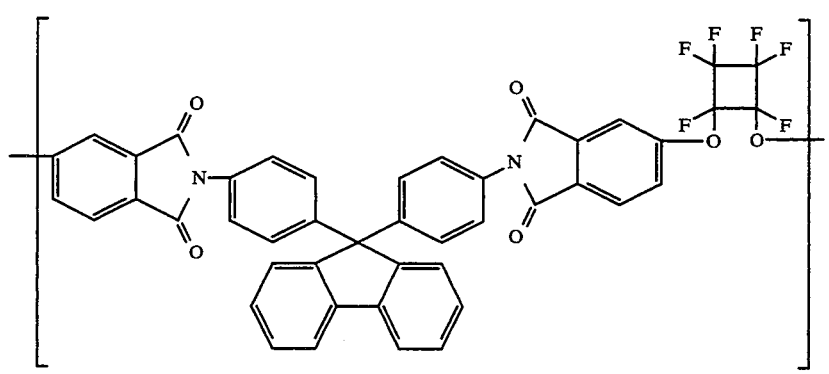

Formula VI

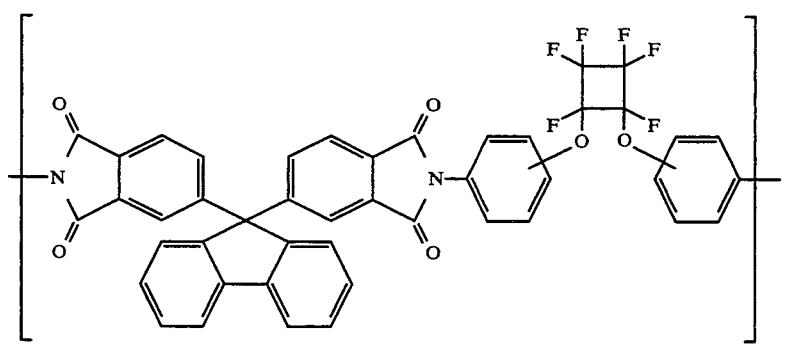

Formula VII with meta or para substituted aniline-ether aromatic rings

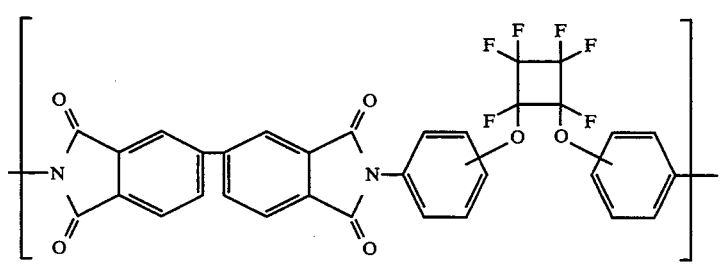

Formula VIII with meta or para substituted aniline-ether aromatic rings

-continued
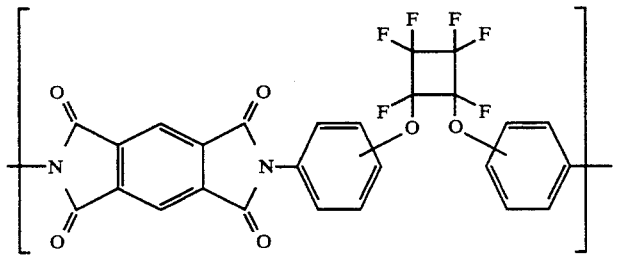
with meta or para substituted aniline-ether aromatic rings
Formula IX
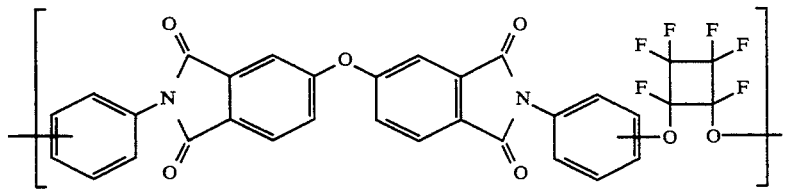
with meta or para substituted aniline-ether aromatic rings
Formula X
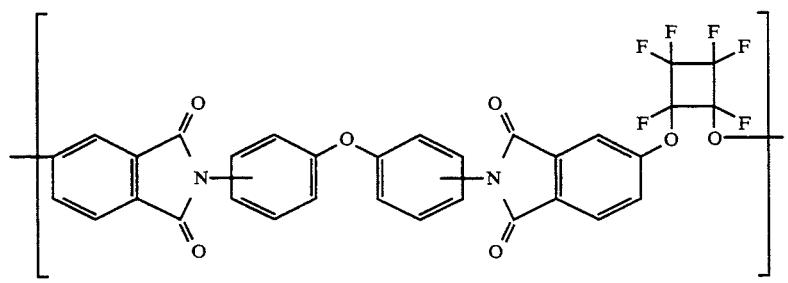
with meta or para substituted imide ethers.
Formula XI
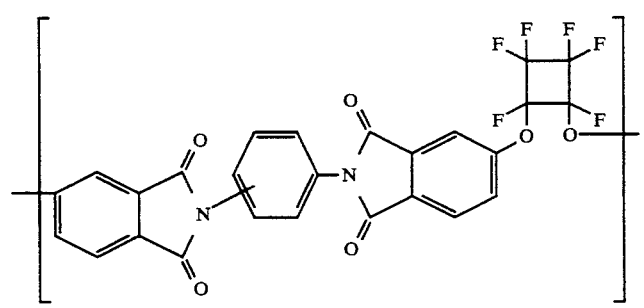
with meta or para substituted phenylenediamine aromatic rings
Formula XII
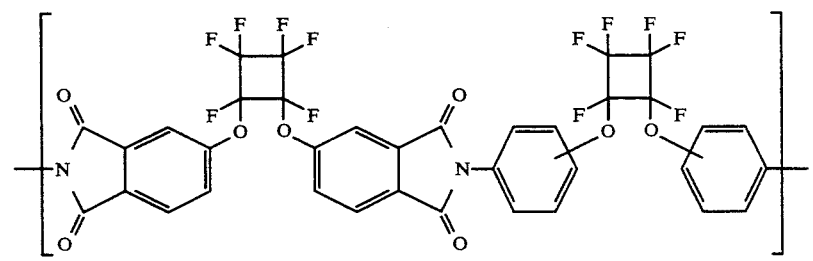
with meta or para substituted aniline-ether aromatic rings
Formula XIII

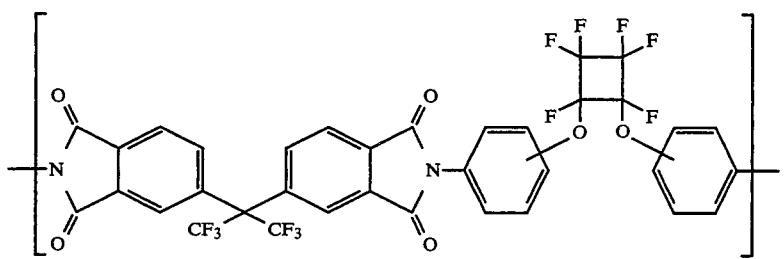
Formula XIV
with meta or para substituted aniline-ether aromatic rings
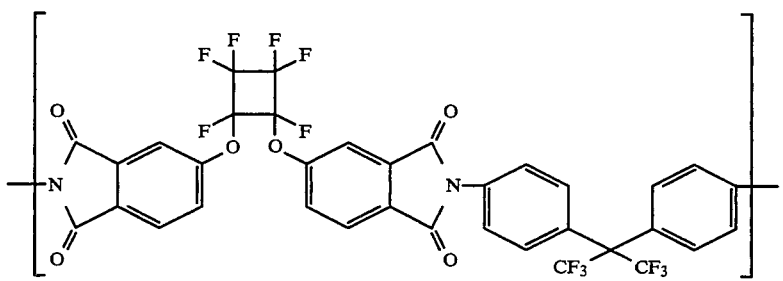
Formula XV
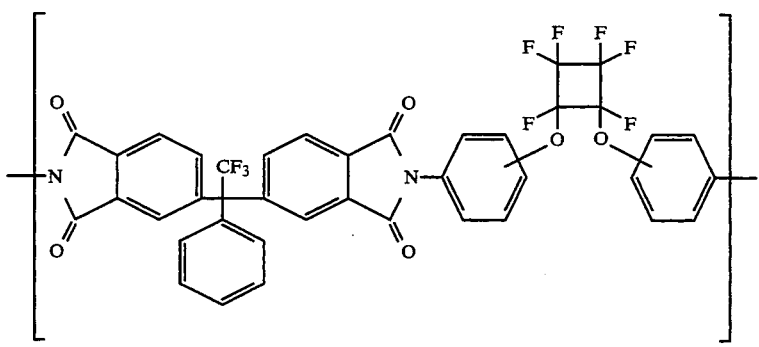
Formula XVI
with meta or para substituted aniline-ether aromatic rings
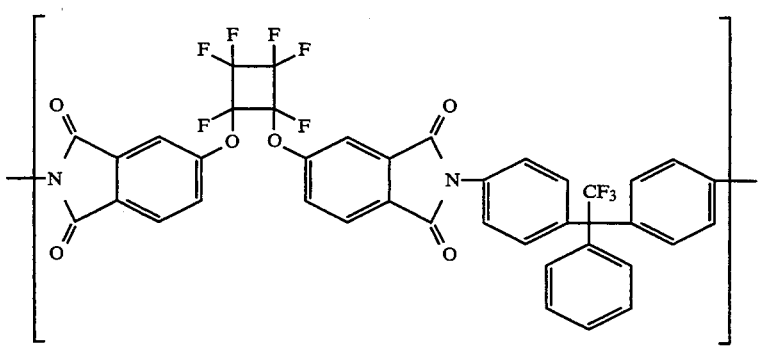
Formula XVII
OR
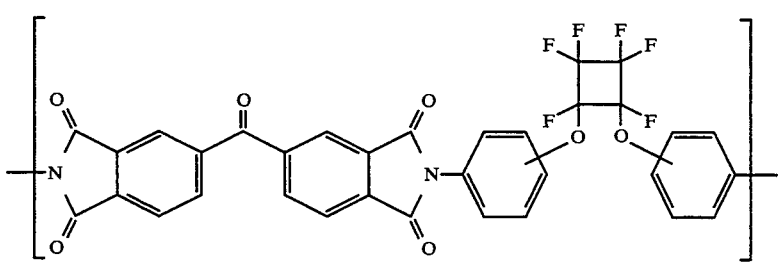
Formula XVIII
with meta or para substituted aniline-ether rings.

21. The process of claim 16 wherein the oligomer has repeating units of a structure represented by at least one of the following formulas:

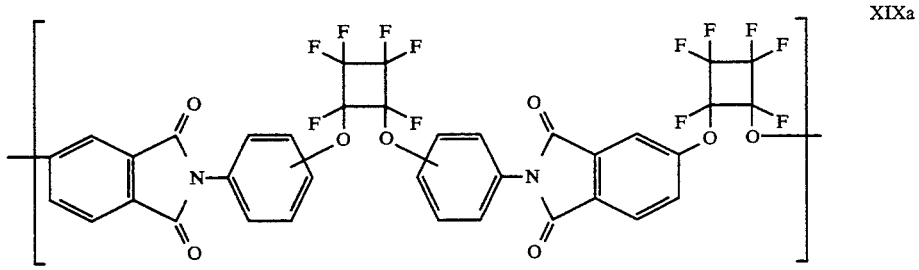

XIXa

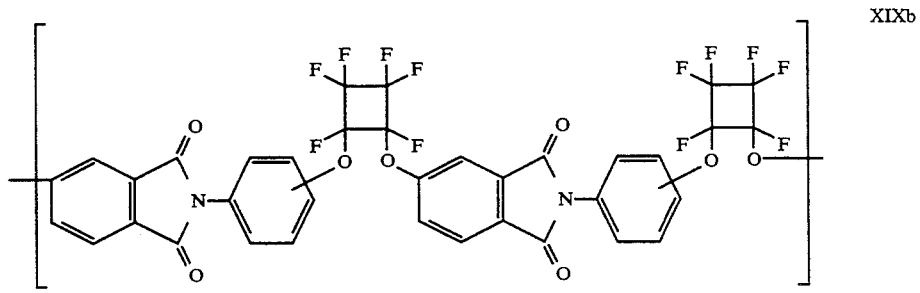

XIXb

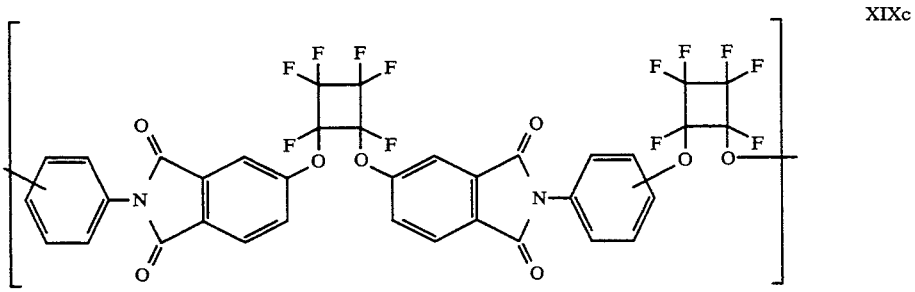

XIXc with ortho or meta substituted aniline ether rings

XIX a, b, and c all with meta or para substituted aniline-ether aromatic rings.

22. A polymer comprising repeating units of at least one of Formula IV or Formula V:

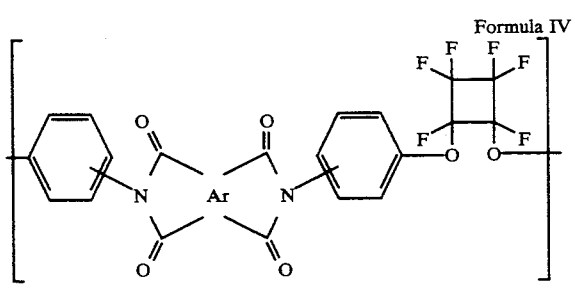

Formula IV

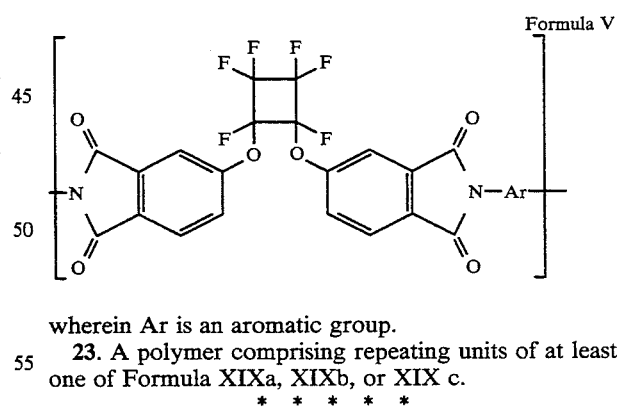

Formula V wherein Ar is an aromatic group;

wherein Ar is an aromatic group.

23. A polymer comprising repeating units of at least one of Formula XIXa, XIXb, or XIX c.

* * * * *